United States Patent [19]
Suzuki et al.

[11] Patent Number: 5,478,856
[45] Date of Patent: * Dec. 26, 1995

[54] STYRENE DERIVATIVES AND SALTS THEREOF

[75] Inventors: Masahiro Suzuki; Kenzi Nozaki; Toshiyuki Hosoya; Takashi Suzuki, all of Hanno; Yuzi Basaki, Iruma; Mitiyo Kozima, Kawagoe; Naosuke Matsuura, Naruto, all of Japan

[73] Assignee: Taiho Pharmaceutical Co., Ltd., Tokyo, Japan

[*] Notice: The portion of the term of this patent subsequent to Mar. 21, 2012, has been disclaimed.

[21] Appl. No.: 256,058

[22] PCT Filed: Oct. 29, 1993

[86] PCT No.: PCT/JP93/01572

§ 371 Date: Jun. 27, 1994

§ 102(e) Date: Jun. 27, 1994

[87] PCT Pub. No.: WO94/10157

PCT Pub. Date: Nov. 5, 1994

[30] Foreign Application Priority Data

Oct. 30, 1992 [JP] Japan ................... 4-333429

[51] Int. Cl.$^6$ .................... A61K 31/42; C07D 261/06
[52] U.S. Cl. .................... 514/378; 514/380; 514/340; 548/247; 548/248; 548/245; 546/275
[58] Field of Search ................... 548/247, 245, 548/248; 514/378, 380, 340; 546/275

[56] References Cited

U.S. PATENT DOCUMENTS 4,327,222   4/1982   Micetich et al. ................... 548/247
4,924,002   5/1990   Kostlan ................... 548/206
4,983,619   1/1991   Gallagher et al. ................... 514/371

OTHER PUBLICATIONS

CA 82: 16724t Isoxazoline . . . –4–ones. Bianchi et al., p. 490, 1975.

CA 115: 135979g Beckmann . . . –1'–ones. Chekti et al., p. 971, 1991.

CA 117: 191833r Preparation . . . inhibitors. Suzuki et al., p. 802, 1992.

CA 118: 254919s Preparation . . . inhibitors. Shindo et al., p. 886, 1993.

Primary Examiner—Joseph K. McKane
Attorney, Agent, or Firm—Nikaido, Marmelstein, Murray & Oram

[57] ABSTRACT

A styrene derivative represented by the formula (1) or a salt thereof:

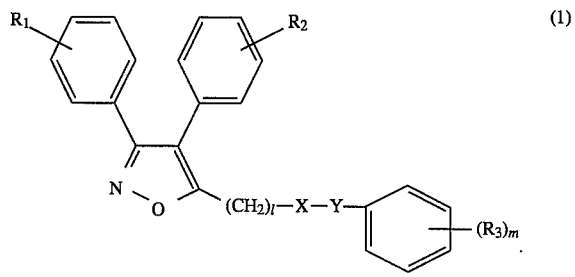

(1)

15 Claims, No Drawings

STYRENE DERIVATIVES AND SALTS THEREOF

This application is a 371 of PCT/JP93/01572 filed Oct. 29, 1993.

TECHNICAL FIELD

The present invention relates to novel styrene derivatives having lipoxygenase inhibiting activity and cyclooxygenase inhibiting activity, salts thereof, and medical use thereof.

BACKGROUND ART

It is considered that leukotrienes produced by lipoxygenase from arachidonic acid and prostaglandins produced by cyclooxygenase from arachidonic acid are deeply concerned in a crisis of allergic asthma, allergic rhinitis, inflammation, etc. Consequently it is desired to inhibit both lipoxygenase and cyclooxygenase in order to strongly and properly inhibit various allergic diseases, inflammations and other diseases. The development of a drug inhibiting both enzymes is earnestly desired.

DISCLOSURE OF THE INVENTION

The present inventors have conducted a research in considering the foregoing problems in the background art, and found that novel styrene derivatives as indicated in the following formula (1) have an excellent lipoxygenase inhibiting activity and an excellent cyclooxygenase inhibiting activity, and are useful as a drug. Thus, the present invention has been accomplished.

The present invention provides styrene derivatives represented by the formula (1) or a salt thereof:

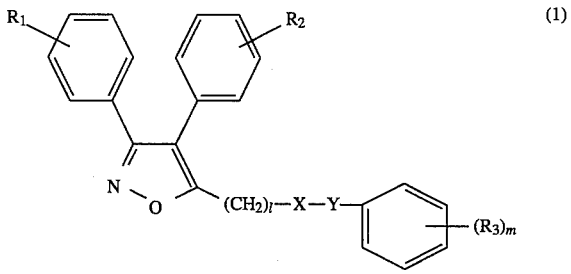

[wherein $R_1$ and $R_2$ are the same or different and each is a hydrogen atom, a lower alkoxy group, a halogen atom or a lower alkyl group; $R_3$ are the same or different and each is a hydroxy group, a lower alkoxy group, a lower alkyl group, a lower alkoxycarbonyloxy group, a lower acyloxy group, a di-loweralkyl phosphate residue or an amino acid residue which may have a protective group; $l$ is an integer of 0 to 5; $m$ is an integer of 0 to 5. X represents a formula —N(Z)CO— {wherein Z represents a formula $(CH_2)_n A$ (wherein A represents a hydrogen atom, a carboxyl group, a di- or mono-loweralkylcarbamoyl group, a carbamoyl group, a lower alkoxycarbonyl group, a cyano group, a lower alkoxy group, a N-acylamino group, a phenyl group which may be substituted, a pyridyl group or a thienyl group, n is an integer of 0 to 5)} or a single bond, Y represents —C(Z')=CH—, —CH=CH—C(Z')=CH—, —C(Z')=CH—CH=CH— (wherein Z' is the same as Z), provided that when n=0, both Z and Z' are not hydrogen atoms, and that when $l$ is 0, X represents a single bond].

The compounds of the present invention represented by the formula (1) has an excellent lipoxygenase inhibiting activity and cyclooxygenase inhibiting activity. Examples of lipoxygenases are 5-lipoxygenase, 12-lipoxygenase and 15-lipoxygenase, etc. The compounds of the invention exhibit, in particular, a potent activity of 5-lipoxygenase inhibition.

The compounds of the invention have excellent lipoxygenase inhibiting and cyclooxygenase inhibiting activities and are useful as antiasthmatic agents, antiallergic agents, agents for treating encephalopathy, cardiovascular agents, agents for treating nephritis, antiinflammatory analgesic agents, antirheumatic agents, agents for treating dermatosis such as psoriasis, and liver disease agents.

Accordingly, the present invention provides antiasthmatic agents, antiallergic agents, agents for treating encephalopathy, cardiovascular agents, agents for treating nephritis, antiinflammatory analgesic agents, anti-rheumatic agents, agents for treating dermatosis such as psoriasis, and liver disease agents, the agents each comprising an effective amount of a compound of the formula (1) given above and a pharmaceutically acceptable carrier therefor.

The present invention also provides a method for treating asthma, allergy, encephalopathy, circulatory diseases, nephritis, inflammation, rheumatism, dermatosis such as psoriasis, and liver diseases which comprises administering an effective amount of a compound of the formula (1) given above to patients.

The present invention is further concerned with the use of compounds of the formula (1) given above in the treatment of asthma, allergy, encephalopathy, circulatory diseases, nephritis, inflammation, rheumatism, dermatosis such as psoriasis, and liver diseases.

Furthermore, the present invention is concerned with the use of compounds of the formula (1) given above in preparing lipoxygenase inhibitor compositions.

Furthermore, the present invention is concerned with the use of compounds of the formula (1) given above in preparing 5-lipoxygenase inhibitor compositions.

Furthermore, the present invention is concerned with the use of compounds of the formula (1) given above in preparing cyclooxygenase inhibitor compositions.

Furthermore, the present invention is concerned with the use of compounds of the formula (1) given above in inhibiting lipoxygenase.

Furthermore, the present invention is concerned with the use of compounds of the formula (1) given above in inhibiting 5-lipoxygenase.

Furthermore, the present invention is concerned with the use of compounds of the formula (1) given above in inhibiting cyclooxygenase.

In accordance with the invention, examples of the halogen atom represented by $R_1$ and $R_2$ are a fluorine atom, a chlorine atom, a bromine atom and an iodine atom. Examples of the lower alkoxy group represented by $R_1$, $R_2$, $R_3$ and A are straight or branched alkoxy groups having 1 to 4 carbon atoms, such as methoxy, ethoxy, n-propoxy, isopropoxy, n-butoxy, isobutoxy, sec-butoxy, tert-butoxy, etc. Examples of the lower alkyl group represented by $R_1$, $R_2$ and $R_3$ are straight or branched alkyl groups having 1 to 4 carbon atoms, such as methyl, ethyl, n-propyl, isopropyl, n-butyl, isobutyl, sec-butyl and tertbutyl etc. Examples of the lower alkoxycarbonyl group represented by A are straight or branched alkoxycarbonyl groups having 2 to 5 carbon atoms, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, etc. Examples of the lower acyloxy group represented by $R_3$ are straight or branched acyloxy groups having 2 to 5 carbon atoms, such as acetyloxy, propanoyloxy, butanoyloxy, 2-methylpropanoyloxy, valeryloxy, etc. Examples of the lower alkoxycarbonyloxy group represented by $R_3$ are straight or branched alkoxycarbonyloxy groups having 2 to 5 carbon atoms, such as methoxycarbonyloxy, ethoxycarbonyloxy, n-propoxycarbonyloxy, isopropoxycarbonyloxy, n-butoxycarbonyloxy, isobutoxycarbonyloxy, sec-butoxycarbonyloxy, tert-butoxycarbonyloxy, etc. Examples of the di-loweralkyl phosphate residue are phosphoric acid residues substituted with two alkyl groups having 1 to 4 carbon atoms, such as dimethyl phosphate residue, diethyl phosphate residue, dipropyl phosphate residue and dibutyl phosphate residue, in particular, groups of the formula —O—P(O)(OR$^o$)$_2$ (wherein R$^o$ is an alkyl group having 1 to 4 carbon atoms). The amino acid residue, which may have a protective group, represented by $R_3$ is a group derived from an amino acid by removal of the hydrogen atom of the carboxyl group thereof. Examples of said amino acid are natural or synthetic amino acids such as glycine, alanine, methionine, valine, serine, proline, leucine, isoleucine, glutamine, histidine, phenylalanine, phenylglycine, etc. Examples of the protective group for amino group of the amino acid are lower alkyl groups having 1 to 6 carbon atoms, lower acyl groups having 2 to 5 carbon atoms, lower alkoxycarbonyl groups having 2 to 5 carbon atoms and a benzyloxycarbonyl group, among others. Examples of the amino acid having a protective group, are N,N-dimethylglycine, N-acetylglycine, N-tert-butoxycarbonylglycine, N-benzyloxycarbonylglycine, N-acetylvaline, N-tert-butoxycarbonylvaline, etc. Examples of the di- or mono-loweralkylcarbamoyl group represented by A are monoalkylcarbamoyl groups having 2 to 5 carbon atoms, such as methylcarbamoyl, ethylcarbamoyl, propylcarbamoyl, butylcarbamoyl and the dialkylcarbamoyl groups having 3 to 9 carbon atoms, such as dimethylcarbamoyl, diethylcarbamoyl, dipropylcarbamoyl, dibutylcarbamoyl, etc. Examples of the N-acylamino group represented by A are straight or branched and aliphatic or aromatic acylamino groups having 2 to 7 carbon atoms, such as acetylamino, propanoylamino, butanoylamino, 2-methylpropanoylamino, valerylamino, benzoylamino, etc. The phenyl group which may be substituted, represents a phenyl group which may have 1–3 substituent groups selected from one or more lower alkyl group, lower alkoxy group, nitro group, halogen atoms such as chlorine, fluorine, bromine, etc. Specifically, tolyl, xylyl, 4-ethylphenyl, p-cumyl, 2-methoxyphenyl, 4-ethoxyphenyl, 4-chlorophenyl, 2-chlorophenyl, 2,4-dichlorophenyl, 3-bromophenyl, etc. Examples of pyridyl groups are 2-pyridyl, 3-pyridyl, 4-pyridyl. Examples of thienyl groups are 2-thienyl, 3-thienyl.

Among the compounds of formula (1) mentioned above, those in which $R_1$ and $R_2$ are lower alkoxy groups, $R_3$ are the same or different and each is a hydroxy group, a lower alkoxy group, a lower alkyl group, a lower alkoxycarbonyloxy group or a lower acyloxy group, X is a group represented by —NHCO—, Y is a group represented by —C(Z')=CH—, —CH=CH—C(Z')=CH— or —C(Z')=CH—CH=CH—, wherein n shown in Z' is 0 to 3, A is a hydrogen atom, a di- or mono-loweralkylcarbamoyl group, a lower alkoxycarbonyl group, a lower alkoxy group or a thienyl group are preferred.

Most preferred are those compounds in which $R_1$ and $R_2$ are lower alkoxy groups, $R_3$ are the same or different and each is a hydroxy group, a lower alkoxy group or a lower alkoxycarbonyloxy group, X is a group represented by —NHCO—, Y is a group represented by —C(Z')=CH— or —C(Z')=CH—CH=CH—, wherein n shown in Z' is 0, A is a di- or mono-loweralkylcarbamoyl group or a lower alkoxycarbonyl group.

Examples of the salts of the styrene compounds of the invention include basic group-derived salts, such as inorganic acid salts, such as hydrochloride, sulfate, nitrate, phosphate, etc. and organic acid salts, such as maleate, succinate, malate, fumarate, p-toluenesulfonate, methanesulfonate, etc., and acid group-derived salts, such as sodium salt, potassium salt, calcium salt, etc.

The compounds of the present invention as represented by formula (1) can be produced by the methods shown below in terms of reaction formulas (i) to (v).

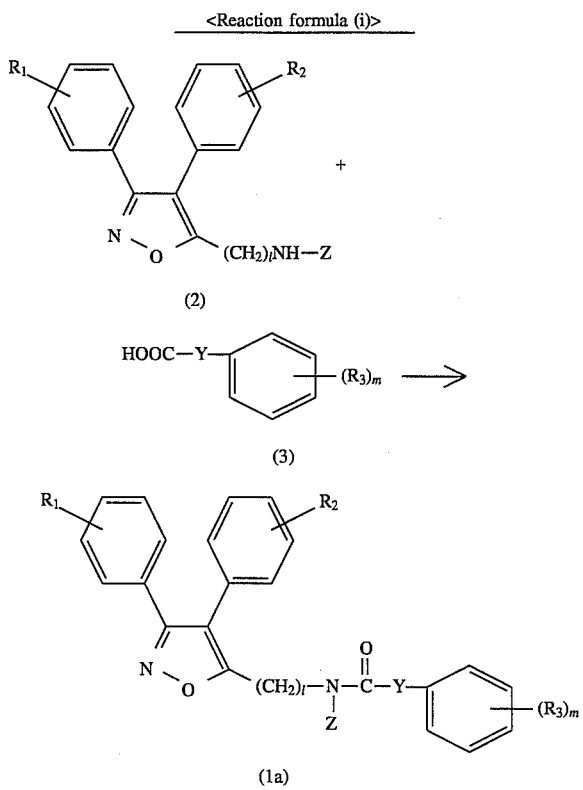

[wherein $R_1$, $R_2$, $R_3$, l, m, Y and Z are as defined above.]

The desired styrene derivatives of formula (1a) can be produced by reacting an amine of formula (2) with a carboxylic acid of formula (3) in a solvent, using a condensing agent, where appropriate in the presence of a catalyst. In cases where $R_3$ in the compound of formula (3) is a hydroxy group, the condensation may be carried out after protection of said group with an appropriate protective group, followed by removing the protective group. The protective group is not limited to any particular species provided that the subsequent deprotection reaction for the elimination thereof will not produce any adverse effect. Thus, methoxyethoxymethyl, methoxymethyl, tetrahydrofuranyl, tetrahydropyranyl and like groups can be used and introduction of these protective groups can be performed by the method described in Journal of American Chemical Society, 100, 8031 (1978). The solvent mentioned above is not limited to any particular species provided that it is inert to the reaction. For example, ethers such as ethyl ether, tetrahydrofuran, etc., halogenated hydrocarbons such as methylene chloride, chloroform, etc., aromatic hydrocarbons such as benzene, toluene, etc., and aprotic polar solvents such as N,N-dimethylformamide, dimethyl sulfoxide, acetonitrile, etc., can be used as a solvent. As examples of the condensing agent, there may be mentioned N,N'-dicyclohexylcarbodiimide, ethyl chlorocarbonate, pivaloyl chloride and chlorosulfonyl isocyanate, among others. The catalyst is, for example, 4-dimethylaminopyridine, 1-hydroxybenzotriazole, pyridine or triethylamine. In carrying out the reaction, the compound of formula (3) is used preferably in an amount of about 1 to about 2 equivalents, the condensing agent in an amount of about 1 to about 3 equivalents, and the catalyst in an amount of about 0.1 to 2 equivalents, relative to the compound of formula (2). The reaction temperature is within the range of ice cooling to around room temperature, and the reaction time is within the range of about 1 to about 48 hours. These conditions are favorable to the progress of the reaction.

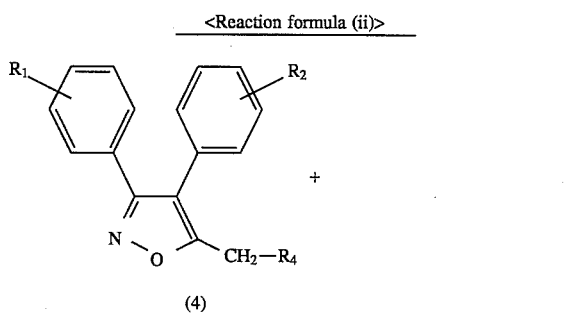

<Reaction formula (ii)>

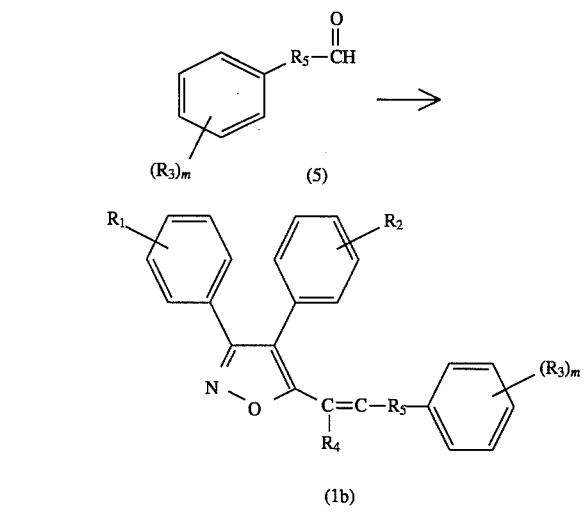

[wherein $R_1$, $R_2$, $R_3$ and m are as defined above. $R_4$ represents a lower alkoxycarbonyl group or a cyano group, $R_5$ represents —CH=CH— or a single bond.]

The objective styrene derivative of formula (1b) can be produced by reacting a compound of formula (4) with an aldehyde of formula (5) with or without a solvent in the presence of a base. As said solvent, methanol, ethanol and like alcohols are exemplified in addition to those specifically mentioned above in relation to the reaction formula (i). Examples of the base are piperidine, pyridine and like organic amines. In carrying out the reaction, the compound of formula (5) is used preferably in an amount of about 1 to about 1.5 equivalents, the base in an amount of about 1 to about 2 equivalents, relative to the compound of formula (4). The reaction temperature is a reflux temperature of a solvent or about 100° to about 150° C. when without a solvent, and the reaction time is within the range of about 2 to about 5 hours. The reaction conditions of reaction formula (ii) are not limited to the conditions mentioned above. The objective styrene derivatives represented by formula (1b) can also be prepared under the conditions of conventional Knoevenagel reaction.

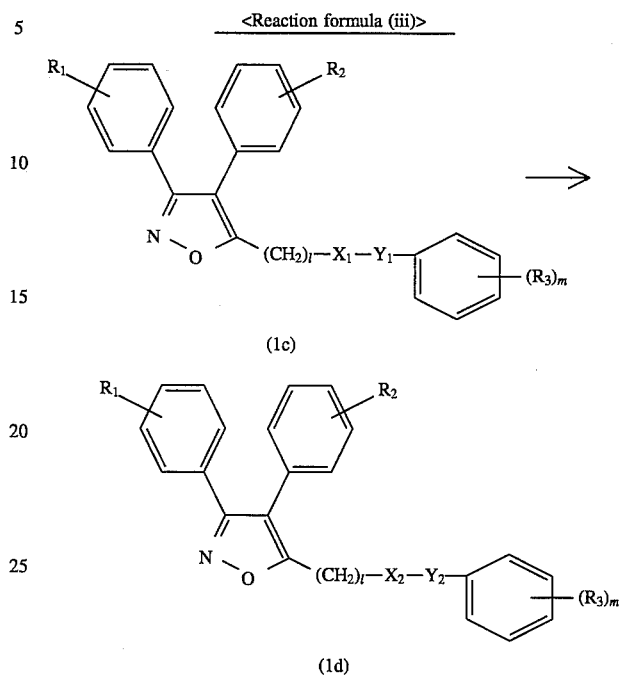

[wherein $R_1$, $R_2$, $R_3$, 1 and m are as defined above. $X_1$ represents a formula —N($Z_1$)CO— {wherein $Z_1$ represents a formula $(CH_2)_nA_1$ (wherein $A_1$ represents a hydrogen atom, a di- or mono-loweralkylcarbamoyl group, a carbamoyl group, a lower alkoxycarbonyl group, a cyano group, a lower alkoxy group, a N-acylamino group, a phenyl group which may be substituted, a pyridyl group or a thienyl group, n is the same as defined above)) or a single bond, $X_2$ represents a formula —N($Z_2$)CO— (wherein $Z_2$ represents a formula $(CH_2)_nA_2$ (wherein $A_2$ represents a hydrogen atom, a di- or mono-loweralkylcarbamoyl group, a carbamoyl group, a carboxyl group, a cyano group, a lower alkoxy group, a N-acylamino group, a phenyl group which may be substituted, pyridyl group or a thienyl group, n is the same as defined above)} or a single bond, $Y_1$ represents —C($Z_1$')=CH—, —CH=CH—C($Z_1$')=CH—, —C($Z_1$')=CH—CH=CH— (wherein $Z_1$' is the same as $Z_1$), $Y_2$ represents — C($Z_2$')=CH—, —CH=CH—C($Z_2$')=CH—, —C($Z_2$')=CH—CH=CH— (wherein $Z_2$' is the same as $Z_2$), provided that when n=0, both $Z_1$ and $Z_1$' are not hydrogen atoms, and that at least one of $X_1$ and $Y_1$ is a lower alkoxycarbonyl group; and provided that when n=0, both $Z_2$ and $Z_2$' are not hydrogen atoms, and that at least one of $X_2$ and $Y_2$ is a carboxyl group.]

The compounds prepared according to the reaction formula (iii) relates to a method for preparing compounds represented by formula (1), wherein A represents a carboxyl group.

The objective compound of formula (1d) can be prepared by alkaline hydrolysis of a compound of formula (1c) in a solvent. Examples of the solvent are a mixed solvent of methanol, ethanol and like alcohols with water, optionally with tetrahydrofuran as an adjunct. Bases used in the alkaline hydrolysis include sodium hydroxide, potassium hydroxide, etc.

In carrying out the invention, the base is used in an amount of about 1 to about 2 equivalents, relative to the compound of formula (1c) to obtain an objective compound of formula (1d). The reaction temperature is ice cooling to around room temperature, and the reaction time is within the range of about 12 to about 48 hours.

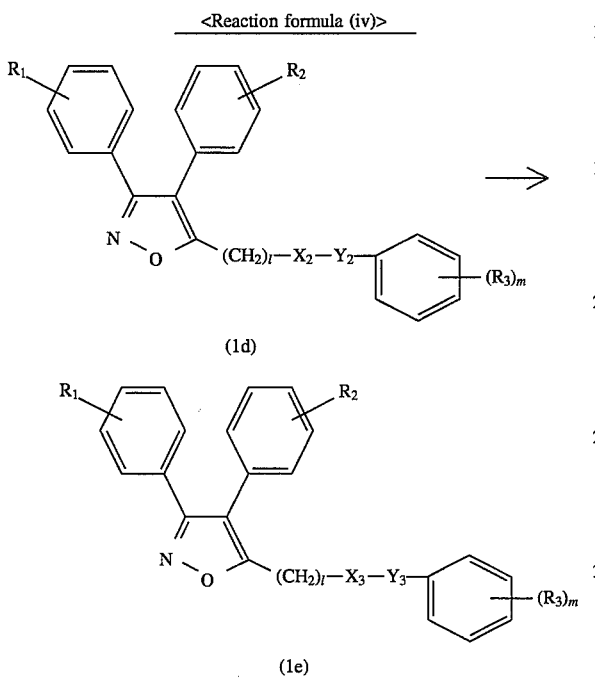

(1d)

(1e)

[wherein $R_1$, $R_2$, $R_3$, $X_2$, $Y_2$, l and m are as defined above. $X_3$ represents a formula —N($Z_3$)CO— {wherein $Z_3$ represents a formula $(CH_2)_n A_3$ (wherein $A_3$ represents a hydrogen atom, a di- or mono-loweralkylcarbamoyl group, a carbamoyl group, a cyano group, a lower alkoxy group, a N-acylamino group, a phenyl group which may be substituted, a pyridyl group or a thienyl group, n is the same as defined above) or a single bond, $Y_3$ represents —C($Z_3'$)=CH—, —CH=CH—C($Z_3'$)=CH—, —C($Z_3'$)=CH—CH=CH— (wherein $Z_3'$ is the same as $Z_3$), provided that when n=0, both $Z_3$ and $Z_3'$ are not hydrogen atoms, and that at least one of $X_3$ and $Y_3$ is a di- or mono-loweralkylcarbamoyl group or a carbamoyl group.]

The compounds produced in this reaction formula relate to a method for producing the compounds of formula (1) wherein A represents a di- or mono-loweralkylcarbamoyl group or a carbamoyl group. Specifically, a compound of formula (1e) is prepared by amidation of a carboxylic acid moiety in $X_2$ and $Y_2$ groups of formula (1d) with an amine compound.

The objective compound of formula (1e) is obtained by reacting the compound of formula (1d) with the amine in the same way as in <reaction formula (i)>. The amines include gaseous ammonia, gaseous methylamine, geseous dimethylamine etc. Further, p-toluenesulfonyl chloride, methanesulfonylchloride are exemplified in addition to the condensing agents used in <reaction formula (i)>

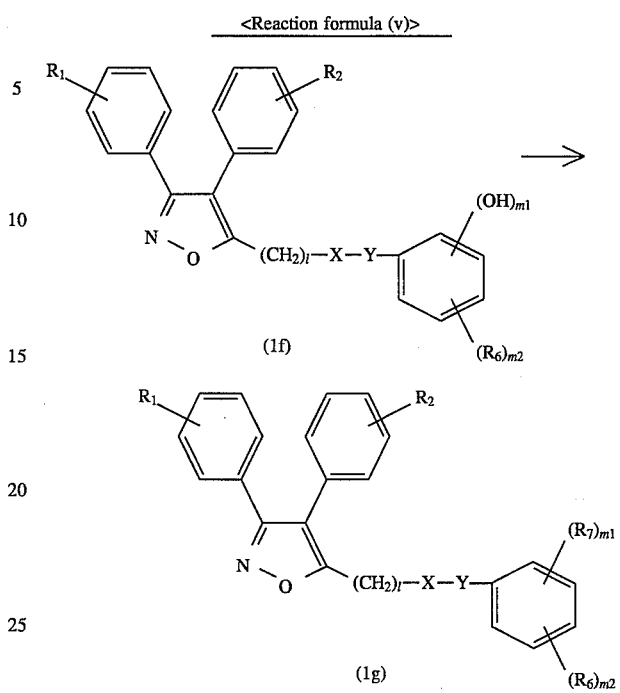

(1f)

(1g)

[wherein $R_1$, $R_2$, X, Y, l are as defined above. $R_6$ represents a lower alkoxy group or a lower alkyl group, $R_7$ represents a lower alkoxycarbonyloxy group, a lower alkylcarbonyloxy group, a di-loweralkyl phosphate residue or an amino acid which may have a protective group, $m_1$ is 1 to 5, $m_2$ is a integer of 0 to 4, $m_1+m_2=m$ (wherein m is an integer of 1 to 5.)]

A desired styrene derivative of formula (1g) is prepared by reacting a compound of formula (1f) with a lower alkoxycarbonyl chloride, (loweralkyl chlorocarbonate), an amino acid or a N-protected amino acid, a lower fatty acid or acid chloride thereof, or a diloweralkylphosphoryl chloride in a suitable solvent using a condensing agent.

Examples of lower alkoxycarbonyl chlorides are methoxycarbonyl chloride, ethoxycarbonyl chloride, n-propoxycarbonyl chloride, isopropoxycarbonyl chloride, n-butoxycarbonyl chloride, isobutoxycarbonyl chloride, sec-butoxycarbonyl chloride, t-butoxycarbonyl chloride and like straight or branched alkoxycarbonyl chloride having 2 to 5 carbon atoms.

Examples of said amino acid are natural or synthetic amino acids, such as glycine, alanine, methionine, valine, serine, proline, leucine, isoleucine, glutamine, histidine, phenylalanine, phenylglycine, etc. Said N-protected amino acids are generally preferable. Any protective group for the amino acid mentioned above can be used as a protective group, specifically N-dimethyl, N-acetyl, N-t-butoxycarbonyl, N-benzyloxycarbonyl are exemplified.

Lower fatty acids include, for example, acetic acid, propionic acid, butyric acid, isobutyric acid, valeric acid, isovaleric acid, pivalic acid and like straight or branched fatty acid having 2 to 5 carbon atoms. Acid chlorides thereof include acetyl chloride, propionyl chloride, butyryl chloride, isobutyryl chloride, valeryl chloride, isovaleryl chloride, pivaloyl chloride and like straight or branched fatty acid chloride having 2 to 5 carbon atoms.

Di-loweralkylphosphoryl chlorides include di($C_1$-$C_4$ alkyl) phosphoryl chlorides such as dimethyl chlorophosphate, diethyl chlorophosphate, dipropyl chlorophosphate, dibutyl chlorophosphate.

The solvent mentioned above is not limited to any particular species provided that it is inert to the reaction. For example, ethers such as ethyl ether, tetrahydrofuran, etc., halogenated hydrocarbons such as methylene chloride, chloroform, etc., aromatic hydrocarbons such as benzene, toluene, etc., and aprotic polar solvents such as N,N-dimethylformamide, dimethyl sulfoxide, etc. can be used as a solvent. When N-protected amino acids or lower fatty acids are used, as examples of the condensing agent, there may be mentioned conventional condensing agents used in a usual peptide synthesis, such as N,N'-dicyclohexylcarbodiimide, ethoxycarbonyl chloride, among others. In this case, additives are optionally added. When the additives including N,N-dimethylaminopyridine and 1-hydroxybenzotriazole and like organic amines are used, the reaction may progress favorably. Bases are generally used as a condensing agent, in the reaction with lower alkoxycarbonyl chloride, lower fatty acid chloride or di-loweralkyl phosphoryl chloride. The bases include organic bases such as pyridine, triethylamine, etc., and inorganic bases such as sodium bicarbonate, potassium bicarbonate, sodium carbonate, potassium carbonate, sodium hydride, etc. In carrying out the reaction, a lower alkoxycarbonyl chloride (lower alkyl chlorocarbonate), an amino acid or a N-protected amino acid, a lower fatty acid or acid chloride thereof, or a di-loweralkyl phosphoryl chlorides is used preferably in an amount of about 1 to about 2.5 equivalents, the condensing agent in an amount of about 1 to about 2.5 equivalents, relative to the compound of formula (1f). When said organic amine is used as additives, the organic amine is used in an amount of about 1 to about 2.5 equivalents, relative to the compound of formula (1f). The reaction time is within the range of about 1 to about 15 hours, and the reaction temperature is within the range of ice cooling to around room temperature to complete the reaction. When a N-protected amino acid is used, the protective group can be removed according to a conventional method, if necessary. Conventional deprotecting agents such as hydrochloric acid, sulfuric acid and like inorganic acids, p-toluenesulfonic acid, trifluoroacetic acid, formic acid and like organic acids can be employed. Deprotection conditions are the same as conditions generally used in the field of peptide synthesis.

The compounds of the invention prepared by the above-mentioned reaction having a basic group can be converted in a form of a salt of the basic group by a conventional method such as reacting the compound with said inorganic acids or organic acids in a solvent such as ethers, lower alcohols, ethyl acetate, hexane, at around room temperature. Further, the compounds of the invention prepared by the above-mentioned reaction having an acidic group can be converted in a form of a salt of the acidic group by a known method such as reacting the compound with alkali metal or alkaline earth metal hydroxide, such as sodium hydroxide, potassium hydroxide, calcium hydroxide, or a strong base such as sodium methoxide, potassium methoxide, sodium hydride in lieu of the inorganic or organic acid mentioned above in such a solvent as mentioned above.

A method for preparing starting materials is described in the examples shown below and an international application PCT/JP92/00571. Preparation of the starting materials can be performed, with reference to a variety of known documents, specifically, according to the following method.

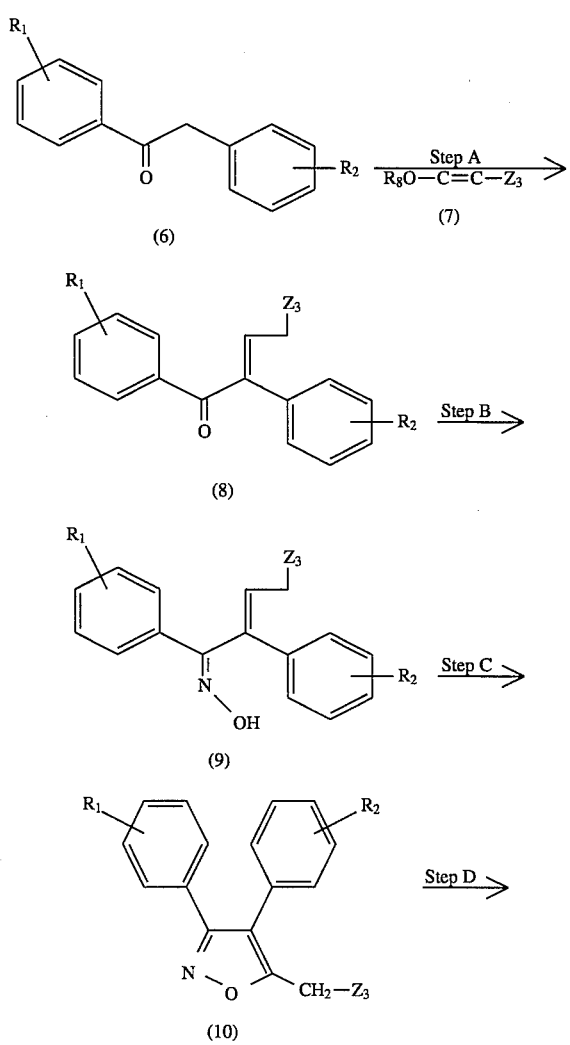

-continued
<Reaction formula (vi)>

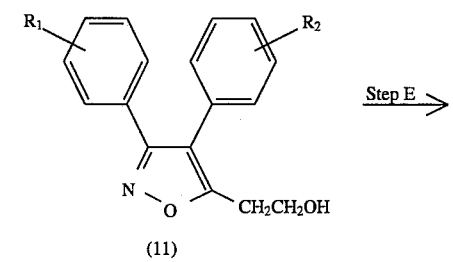

(11)

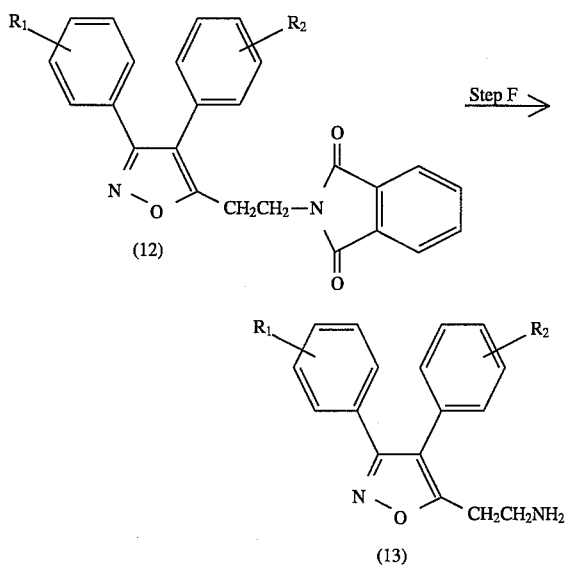

[wherein $R_1$ and $R_2$ are as defined above. $R_8$ represents a lower alkyl group, $Z_3$ represents a lower alkoxycarbonyl group or a nitrile group.]

(Step A)

A compound of formula (8) is prepared by reacting a deoxybenzoin derivative of formula (6) with an alkoxyacrylonitrile or alkoxyacrylic acid derivative of formula (7) in an appropriate solvent in the presence of a base.

As the lower alkyl group represented by $R_8$, those lower alkyl groups specifically mentioned hereinabove are exemplified. Examples of the lower alkoxycarbonyl group represented by $Z_3$ are straight or branched alkoxycarbonyl groups having 2 to 5 carbon atoms, such as methoxycarbonyl, ethoxycarbonyl, n-propoxycarbonyl, isopropoxycarbonyl, n-butoxycarbonyl, isobutoxycarbonyl, tert-butoxycarbonyl, etc.

Examples of said solvent are alcohols such as methanol, ethanol, tert-butanol, etc., ethers such as ethyl ether, tetrahydrofuran, etc., aromatic hydrocarbons such as benzene, toluene, etc., halogenated hydrocarbons such as carbon tetrachloride, chloroform, etc., and aprotic polar solvents such as N,N-dimethylformamide, dimethyl sulfoxide, etc. Examples of the base are alkaline bases such as sodium hydroxide, potassium hydroxide, sodium hydride, sodium amide, sodium methoxide, potassium tert-butoxide, butyllithium, etc., and organic bases such as triethylamine, diethylaminopyridine, pyridine, etc. In carrying out the reaction, the compound of formula (7) is preferably used in an amount of about 1 to 3 equivalents, and the base in an amount of about 0.1 to 3 equivalents, relative to the compound of formula (6). For advantageous progress of the reaction, the reaction temperature is within the range of ice cooling to around the boiling point of the solvent, and the reaction time is about 0.5 to 20 hours.

(Step B)

The compound of formula (8) obtained in step A is reacted with hydroxylamine or a salt thereof in an appropriate solvent to give a compound of formula (9) Examples of hydroxylamine salts to be added to the reaction is not limited to any particular species but includes hydrochloride and sulfate thereof that are commercially available, for instance. The solvent is not limited to any particular species provided that it is inert to the reaction. Thus, for example, those specifically mentioned in relation to step A can be used. Hydroxylamine or a salt thereof is preferably used in an amount of about 1 to 10 equivalents relative to the compound of formula (8). For advantageous progress of the reaction, the reaction temperature is about room temperature to the boiling point of the solvent and the reaction time is about 1 to 30 hours. In carrying out the reaction, an acid or base may be added as necessary. Further, the reaction may be carried out in a solvent such as a buffer solution.

(Step C)

The compound of formula (9) is subjected to cyclization in an appropriate solvent using a halogenating agent or the like, or to reaction with an oxidizing agent in an appropriate solvent or without solvent to give a compound of formula (10). The solvent is not particularly limited provided that it is inert to the reaction. Thus, for example, those solvents specifically mentioned in relation to step A can be used. Acetic acid or the like can also be used. The halogenating agent to be used in the cyclization reaction is, for example, chlorine, bromine, iodine, N-chlorosuccinimide or N-bromosuccinimide. The halogenating agent is preferably used in an amount of about 1 to 3 equivalents relative to the compound of formula (9). For advantageous progress of the reaction, the reaction temperature is about −70° to 150° C. and the reaction time is about 1 to 24 hours.

Examples of the oxidizing agent are oxides such as potassium permanganate, manganese dioxide, potassium periodate, etc., metal salts such as lead tetraacetate, mercury acetate, etc., peroxides such as hydrogen peroxide, peracetic acid, etc. In addition to the method using these oxidizing reagents, oxygen oxidation methods using air or oxygen or organic electrolytic oxidation methods utilizing anodic oxidation, for instance, can also give the compound of formula (10).

In the reaction using an oxidizing agent, the oxidizing agent is preferably used in an amount of about 0.2 to 10 equivalents relative to the compound of formula (9). For advantageous progress of the reaction, the reaction temperature is within the range of ice cooling to about 100° C. and the reaction time is within the range of about 5 minutes to about 10 hours.

In the oxygen oxidation and organic electrolytic oxidation methods, a reaction temperature of about −20° C. to about 100° C. and a reaction time of about 5 minutes to about 10 hours are favorable for the progress of the reaction. It is generally known that the reactions can progress efficiently in the presence of a catalyst. The catalyst is preferably used in an amount of about $1 \times 10^{-5}$ to 10 equivalents relative to the compound of formula (9). Examples of the catalyst are cobalt, rhodium, palladium, copper, cerium, ruthenium and like metals, metal compounds such as metal salts, metal oxides, metal complexes, etc.

(Step D)

A compound of formula (10) in which $Z_3$ is a nitrile group is subjected to solvolysis or hydrolysis in the presence of an acid or base to give a corresponding carboxylic acid, which is esterified and further reduced to give a compound of formula (11). The solvolysis or hydrolysis can be effected by the solvolysis method described in Japanese Unexamined Patent Publication No. 60-75471 or by a hydrolysis method conventional in the relevant field of art. The acid to be used in the solvolysis or hydrolysis reaction include inorganic acids such as hydrochloric acid, sulfuric acid, nitric acid, etc. and bases include inorganic bases such as sodium hydroxide, potassium hydroxide, sodium carbonate, etc. The esterification can be carried out by a method known in the art, for example, in an alcohol solvent such as methanol or ethanol using an acid as a catalyst. Said acid is, for example, an inorganic acid such as hydrochloric acid or sulfuric acid, or an organic acid such as p-toluenesulfonic acid.

The reduction of the ester can be carried out in an appropriate solvent using a reducing agent. The solvent may be any of those solvents specifically mentioned in relation to step A. The reducing agent is, for example, lithium aluminum hydride, sodium borohydride or the like. The reducing agent is preferably used in an amount of about 1 to 10 equivalents relative to the ester. For advantageous progress of the reaction, the reaction temperature is within the range of ice cooling to around room temperature and the reaction time is about 10 minutes to about 24 hours.

A compound of formula (10) in which $Z_3$ is a lower alkoxycarbonyl group, when subjected to reduction in the same manner as mentioned above, gives a compound of formula (11).

The intermediate ($Z_3$ being carboxylic acid) in this process can also be prepared by the method described in Japanese Unexamined Patent Publication No. 56-59764.
(Step E)

The alcohol of formula (11) is reacted with phthalimide, triphenylphosphine and diethyl azodicarboxylate in an appropriate solvent to give a compound of formula (12)o As the solvent, there may be mentioned ethers such as diethyl ether, tetrahydrofuran, etc., halogenated hydrocarbons such as methylene chloride, chloroform, etc., and aromatic hydrocarbons such as benzene, toluene, etc.

Preferably, phthalimide, triphenylphosphine and diethyl azodicarboxylate are used each in an amount of about 1 to 2 equivalents relative to the alcohol of formula (11). For advantageous progress of the reaction, the reaction temperature is within the range of ice cooling to around room temperature and the reaction time is about 1 to 48 hours.
(Step F )

The compound of formula (12) is treated under the conditions generally employed for the Gabriel reaction to give a compound of formula (13). For advantageous progress of the reaction, hydrazine hydrate is used in an amount of about 1 to 1.1 equivalents relative to the compound of formula (12) and the reaction is carried out in ethanol at room temperature to the vicinity of the boiling point of ethanol for about 1 to 24 hours.

The objective amine can also be prepared by conventional acid or alkaline hydrolysis.

<Reaction formula (vii)>

(6) Step G →

-continued
<Reaction formula (vii)>

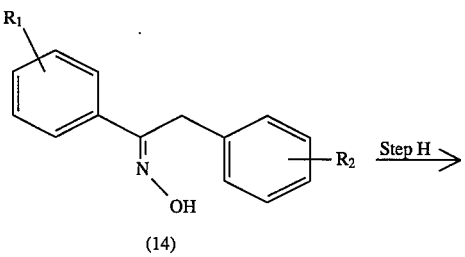
(14)

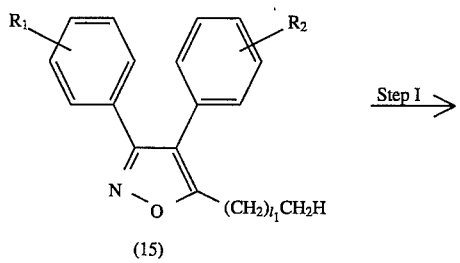
(15)

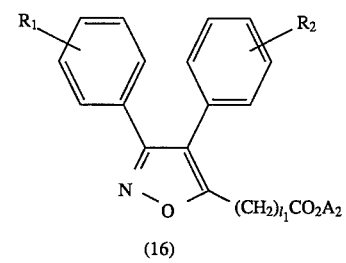
(16)

[wherein $R_1$, $R_2$ and $A_2$ are as defined above. $l_1$ is 3 to 5.]
(Step G )

A compound of formula (14) can be prepared by the same oxime formation method as in the above mentioned step B in reaction formula (vi).
(Step H)

The compound of formula (14) is reacted with an alkyllithium or phenyllithium in a solvent and further reacted with an acid anhydride to give a carboxylic acid of formula (15). The solvent mentioned above is not specifically limited provided that it is inert to the reaction. Thus, ethers such as ethyl ether, tetrahydrofuran, etc., saturated alkyls such as hexane, cyclohexane, etc., and halogenated hydrocarbons such as chloroform, methylene chloride, etc., may be used. The alkyllithium is, for example, methyllithium, n-butyllithium, sec-butyllithium or tert-butyllithium. The acid anhydride is, for example, succinic anhydride, glutaric anhydride, adipic anhydride, heptanedioic anhydride or the like. For advantageous progress of the reaction, the alkyllithium or phenyllithium is used in an amount of about 2 to 3 equivalents, and acid anhydride in an amount of about 1 to 2 equivalents relative to the compound of formula (14), and the reaction is carried out preferably under an inert dry gas atmosphere such as nitrogen or argon. For advantageous progress of the reaction, the reaction temperature is about −20° C. to around room temperature and the reaction time is about 1 to 2 hours for the reaction with the alkyllithium or phenyllithium and about 0.5 to 2 hours for the reaction with the acid anhydride.
(Step I)

A compound of formula (16) can be prepared in the same manner of esterification as used above in Step D in reaction formula (vi).

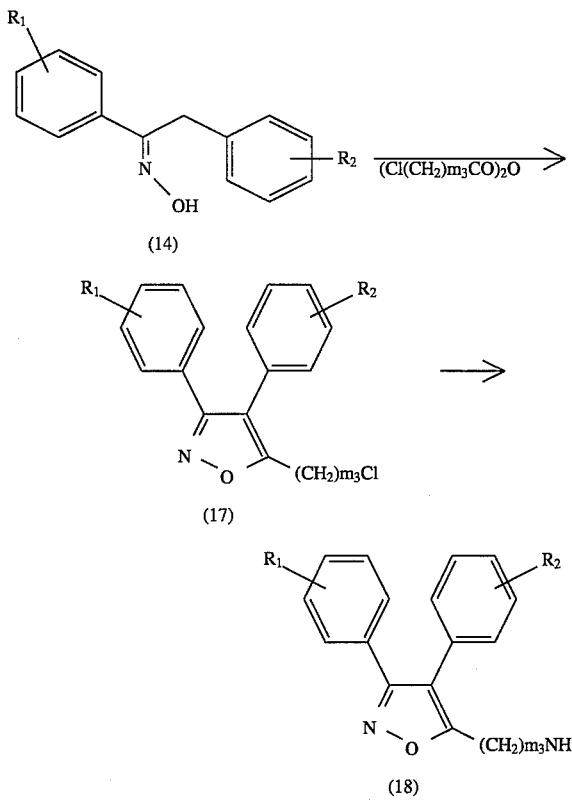

[wherein $R_1$ and $R_2$ are as defined above. $m_3$ is 1 to 5.]

A compound of formula (17) is prepared by reacting a compound of formula (14) with an alkyllithium or phenyllithium in a solvent, followed by reacting with ω-chlorolower fatty acid anhydride such as bis(chloro acetic) anhydride, bis(chloropropionic) anhydride. The solvent mentioned above is not specifically limited provided that it is inert to the reaction. Thus, ethers such as ethyl ether, tetrahydro-furan, etc., saturated alkyls such as hexane, cyclo-hexane, etc. may be used. The alkyllithium is, for example, methyllithium, n-butyllithium, sec-butyllithium or tert-butyllithium. For advantageous progress of the reaction, the alkyllithium or phenyllithium is used in an amount of about 2 to 3 equivalents, and the ω-chlorolower fatty acid anhydride in an amount of about 1 to 2 equivalents relative to the compound of formula (14). The reaction is carried out preferably under an inert dry gas atmosphere such as nitrogen or argon. For advantageous progress of the reaction, the reaction temperature is about −20° C. to around room temperature and the reaction time is about 1 to 2 hours for the reaction with the alkyllithium or phenyllithium and about 0.5 to 2 hours for the reaction with the ω-chlorolower fatty acid anhydride.

A compound of formula (18) is prepared by reacting a compound of formula (17) with an ammonia in a solvent. The solvent mentioned above is not specifically limited provided that it is inert to the reaction. Thus, alcohols such as methanol, ethanol etc., and water may be used. Ammonia is employed by blowing an ammonia gas into the solvent mentioned above or as an aqueous ammonia. The ammonia is used in an excessive amount relative to the compound of formula (17). For advantageous progress of the reaction, the reaction temperature is about room temperature to the boiling point of the solvent and the reaction time is about 2 to 12 hours.

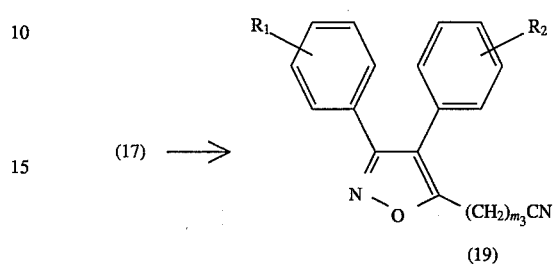

[wherein $R_1$, $R_2$ and $m_3$ are as defined above.]

A compound of formula (19) is prepared by reacting a compound of formula (17) with an alkali cyanide in a solvent. As a solvent, dimethylsulfoxide, N,N-dimethylformamide and water are used individually or in a mixture thereof. For advantageous progress of the reaction, potassium cyanide or sodium cyanide are used in an amount of about 1.5 to 3 equivalents, relative to the compound of formula (17) at about room temperature for about 12 to 24 hours.

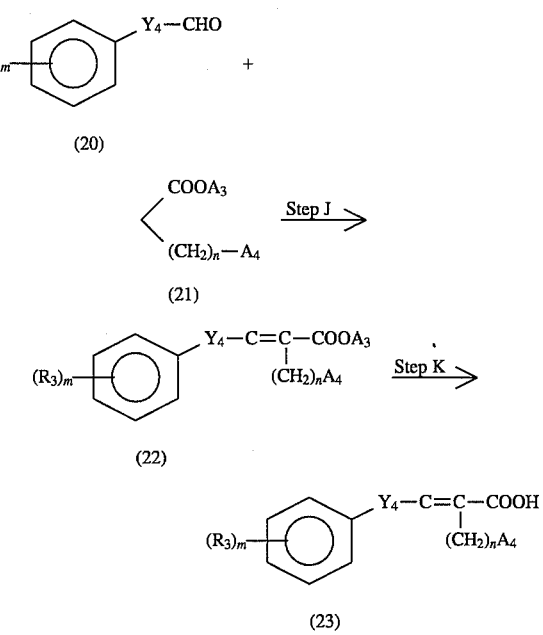

[wherein $R_3$, m and n are as defined above. $A_3$ represents a lower alkyl group, a β-methoxyethoxymethyl group or a methoxymethyl group. $A_4$ represents a hydrogen atom (provided that n is not 0.), mono- or di-loweralkylcarbamoyl group, a carbamoyl group, a lower alkoxycarbonyl group, a cyano group, a lower alkoxy group, a phenyl group which may be substituted, a pyridyl group or a thienyl group. $Y_4$ represents a single bond or a group of formula —CH=C(Z)— (wherein Z is as defined above).]

(Step J)

A compound of formula (22) is obtained by reacting a compound of formula (20) with a compound of formula (21) in a solvent in the presence of an acid or a base. The solvent mentioned above is not specifically limited provided that it is inert to the reaction. Thus, alcohols such as methanol, ethanol, etc., ethers such as ethyl ether, tetrahydrofuran, etc., and aromatic hydrocarbons such as benzene, toluene, etc. may be used. The base includes sodium hydride, potassium-t-butoxide, piperidine, pyridine, etc. The acid includes p-toluenesulfonic acid, hydrochloric acid, sulfuric acid, etc. In carrying out the reaction, the compound of formula (21) is preferably used in an amount of about 1 to 1.5 equivalents, the base and acid in an amount of about 0.1 to 2 equivalents relative to the compound of formula (20). For advantageous progress of the reaction, the reaction temperature is about room temperature to the boiling point of the solvent and the reaction time is about 1 to 48 hours.

(Step K)

A compound of formula (23) is obtained by alkaline hydrolysis of a compound of formula (22) in the same way as reaction formula (iv). With respect to the compound in which $A_3$ is a β-methoxyethoxymethyl or methoxymethyl group, the compound of formula (23) is prepared by using an acid catalyst in a solvent. Said solvent includes ethers such as ethyl ether, tetrahydrofuran, etc., and alcohols such as methanol, ethanol, etc. The acid includes p-toluenesulfonic acid, hydrochloric acid, sulfuric acid, etc.

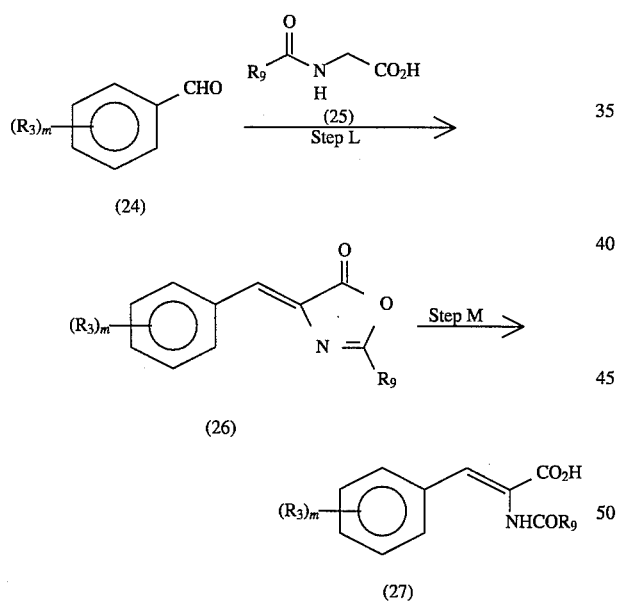

[wherein $R_3$ and m are as defined above. $R_9$ represents a lower alkyl group or a phenyl group.]

The following Step L and Step M are performed according to a method described in Synthesis, 793 (1992).

(Step L)

An objective compound of formula (26) is obtained by reacting a compound of formula (24) with a compound of formula (25) in acetic anhydride in the presence of sodium acetate. In carrying out the reaction, the compound of formula (25) is preferably used in an amount of about 1 to 1.5 equivalents, sodium acetate in an amount of about 1 to 1.5 equivalents and acetic anhydride in an amount of about 5 to 10 equivalents relative to the compound of formula (24). For advantageous progress of the reaction, the reaction temperature is about 90° to 120° C. and the reaction time is about 2 to 8 hours.

(Step M)

A compound of formula (27) is obtained by reacting either in a solvent of acetone-water with sodium acetate or with 0.2N hydrochloric acid. In carrying out the reaction, sodium acetate is preferably used in an amount of about 1 to 1.5 equivalents relative to the compound of formula (26), and a 0.2N hydrochloric acid is preferably used 5 to 20 ml relative to 1 mmol of the compound of formula (26). For advantageous progress of the reaction, the reaction temperature is about boiling point of the solvent and the reaction time is about 0.5 to 1.5 hours.

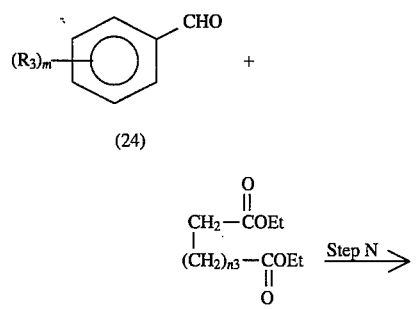

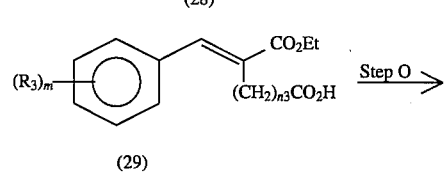

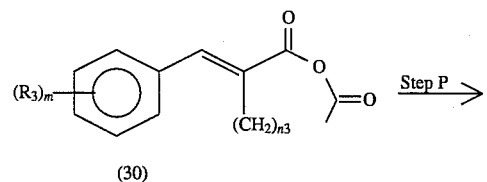

[wherein $R_3$ and m are as defined above. $n_3$ is 1 to 5. $A_5$ represents a lower alkoxycarbonyl group, a carbamoyl group or a di- or mono-loweralkylcarbamoyl group.]

(Step N)

A compound of formula (29) is obtained by reacting a compound of formula (24) with a diester of formula (28) in a solvent in the presence of a base. The solvent mentioned above is not specifically limited provided that it is inert to the reaction. Thus, ethers such as ethyl ether, tetrahydrofuran, etc. are exemplified as a solvent. The base includes sodium hydride, potassium-t-butoxide, etc. In carrying out the reaction, the base is used in an amount of about 1 to 2 equivalents relative to the compound of formula (28) for advantageous progress of the reaction. The reaction temperature is about room temperature to the boiling point of the solvent and the reaction time is about 6 to 4 hours.

Examples of the diester of formula (28) are diethyl succinate, diethyl glutarate, diethyl adipate, diethyl pimelate, etc.

(Step O)

A compound of formula (30) is produced by treating a compound of formula (29) with a condensing agent in a solvent in the presence of a base and dimethylamine or a hydrochloride thereof. The solvent, condensing agent and base described in reaction formula (i) can also be used in this step. The reaction can be performed advantageously in the same conditions as the reaction formula (i) with respect to proportion of reagents, temperature and time.

(Step P)

A compound of formula (31) is obtained by reacting a compound of formula (30) in a solvent with either an amine or an alcohol in the presence of an acid. The solvent mentioned above is not specifically limited provided that it is inert to the reaction. Thus, ethers such as ethyl ether, tetrahydrofuran, etc., halogenated hydrocarbons such as chloroform, methylenechloride, etc., aromatic hydrocarbons such as benzene, toluene, etc. can be exemplified. Examples of the amine are gaseous ammonia, gaseous methylamine, gaseous dimethylamine, gaseous diethylamine, etc. Examples of the alcohol are methanol, ethanol, propanol, 2-propanol, butanol, sec-butanol, t-butanol, etc. The amine or alcohol is preferably employed in an amount equivalent to or excess of a compound of formula (30). For advantageous progress of the reaction, the reaction temperature is ice cooling to room temperature, and reaction time is about 1 to 24 hours.

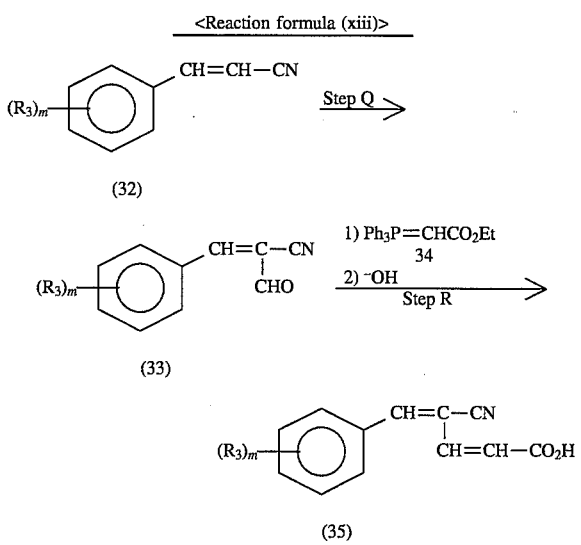

[wherein $R_3$ and m are as defined above.]

(Step Q)

The compound of formula (33) is obtained by reacting a compound of formula (32) with a base in a solvent, subsequently reacted with an electrophile. The solvent mentioned above is not specifically limited provided that it is inert to the reaction. Thus, ethers such as ethyl ether, tetrahydrofuran, etc. are exemplified. Examples of the base are n-butyllithium, sec-butyllithium, tert-butyllithium, lithiumdiisopropylamide, lithiumtetramethylpiperidide, etc. Examplers of the electrophile are methyl formate, ethyl formate, N,N-dimethylformamide, N-formylpiperidine, etc. The reaction is carried out preferably using the base in an amount of about 1 to 2 equivalents, and the electrophile in an amount of 1 to 2 equivalents relative to the compound of formula (32). For advantageous progress of the reaction, the reaction temperature is about −78° C. to −50° C. and the reaction time is about 30 to 60 minutes for the reaction of a compound of formula (32) with the base and is about 1 to 2 hours with the electrophile.

(Step R)

An ethylester of a compound of formula (35) is produced by reacting a compound of formula (33), in a solvent, with carbethoxymethylenetriphenylphosphorane (34). The obtained product is subjected to an alkaline hydrolysis to obtain a compound of formula (35). The solvent mentioned above is not specifically limited provided that it is inert to the reaction. Thus, ethers such as ethyl ether, tetrahydrofuran, etc. are exemplified. The reaction is carried out preferably using the compound of formula (34) in an amount of about to 5 equivalents relative to the compound of formula (33). For advantageous progress of the reaction, the reaction temperature is ice cooling to room temperature and the reaction time is about 12 to 48 hours.

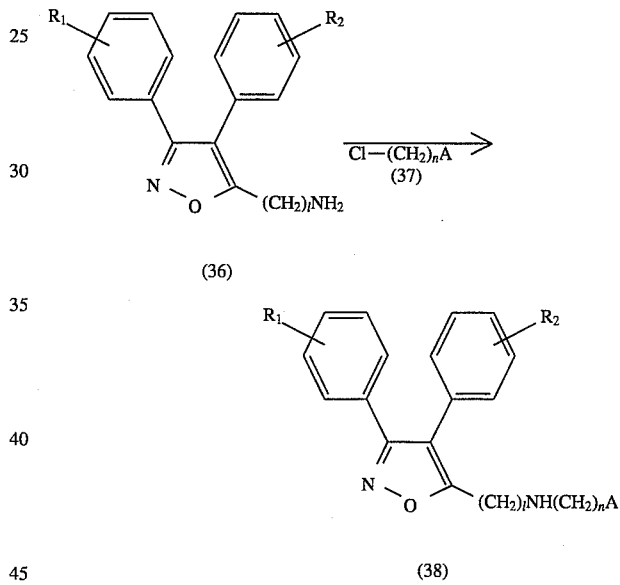

[wherein $R_1$, $R_2$, l, n and A are as defined above.]

An ethylester of a compound of formula (38) is obtained by reacting a compound of formula (36) with ω-chloro compound (37) in a solvent, optionally in the presence of a base. The solvent mentioned above is not specifically limited provided that it is inert to the reaction. Thus, ethers such as ethyl ether, tetrahydrofuran, etc., aromatic hydrocarbons such as benzene, toluene, etc., are exemplified. Examples of the base are triethylamine, dimethylaminopyridine, etc. The reaction is carried out preferably using the ω-chloro compound (37) in an amount of about 0.5 to 1 equivalents, and the base in an amount of 1 to 2 equivalents relative to the compound of formula (36). For advantageous progress of the reaction, the reaction temperature is around room temperature to boiling point of the solvent and the reaction time is about 1 to 8 hours.

The compounds produced in any of the above-mentioned reaction formulas (i) to (xiv) can be isolated and purified by means generally employed in the relevant field of art, for example by concentration, filtration, recrystallization, various chromatographic techniques and so forth.

For use as medicaments, the compounds of the present invention can be made into various pharmaceutical dosage forms according to a preventive or therapeutic purpose. Examples of pharmaceutical dosage forms are oral preparations, injections, suppositories, external preparations (e.g. cataplasm, tape, and like plasters, ointments, cream, lotion) and so on. Such preparations can be formulated in a manner already known or conventional to those skilled in the art.

For the formulation of solid preparations for oral administration, an excipient and, when required, a binder, disintegrator, lubricant, coloring agent, corrigent, flavor, etc. are added to the compound of the invention, and then a preparation is formulated in a usual way as tablets, coated tablets, granules, powders, capsules, or the like, Such additives are those already known in the art, and useful examples are excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dried starch, sodium alginate, agar powder, sodium hydrogen carbonate, calcium carbonate, sodium lauryl sulfate, stearic acid monoglyceride and lactose; lubricants such as purified talc, stearic acid salt, borax and polyethylene glycol; corrigents such as sucrose, bitter orange peel, citric acid and tartaric acid, etc.

For the formulation of liquid preparations for oral administration, a corrigent, buffer, stabilizer, flavor, etc. can be added to the compound of the present invention, and the mixture can be formulated in a usual way into an oral liquid preparations, syrup, elixir or the like. Examples of useful corrigents are those exemplified above. Examples of buffers are sodium citrate, etc. Examples of stabilizers are tragacanth, gum arabic, gelatin, etc.

Injections can be prepared as a subcutaneous, intramuscular or intravenous injection in a conventional way by adding to the compound of the invention a pH adjusting agent, buffer, stabilizer, isotonic agent, local anesthetic, etc. Examples of pH adjusting agents and buffers are sodium citrate, sodium acetate, sodium phosphate, etc. Examples of stabilizers are sodium pyrosulfite, EDTA, thioglycolic acid, thiolactic acid, etc. Examples of local anesthetics are procaine hydrochloride, lidocaine hydrochloride, etc.

Suppositories can be prepared in a usual manner by adding to the compound of the invention a pharmaceutically acceptable carrier already known in the art, such as polyethylene glycol, lanolin, cacao fat and oil, fatty acid triglyceride and, if desired, a surfactant, for example, tween (registered trademark).

Ointments can be prepared in a usual manner by blending to the compound of the invention a base, a stabilizer, a wetting agent, a preservative etc., which are generally used, and the resulting composition is admixed to give an ointment preparation. Examples of the base are liquid paraffin, white petrolatum, white beeswax, octyldodecyl alcohol, paraffin, etc. Examples of the preservative are methyl parahydroxybenzoate, ethyl parahydroxybenzoate, propyl parahydroxybenzoate, etc.

Plasters can be prepared in a usual manner by applying the ointments mentioned above, creams, gels, pastes, etc. to conventional supports. Examples of said supports are suitably woven fabrics and unwoven fabrics made of cotton, staple fiber or some other chemical fiber, films or foamed sheets made of plasticized polyvinyl chloride, polyethylene, polyurethane, etc.

The amount of the compound of the present invention to be incorporated into each of the dosage units varies with the symptoms of the patient or with the type of the preparations. The preferable amount per administration unit is about 1 to 1,000 mg for oral preparations, about 0.1 to 500 mg for injections, or about 5 to 1,000 mg for suppositries. The dosage per day of the drug in the above dosage form is variable with the symptoms, body weight, age, sex and other factors of the patient, but usually ranges from about 0.1 to 5,000 mg, preferably from about 1 to 1,000 mg for human adult. The preparation is preferably administered in a single dose or in two to four devided doses.

EXAMPLES

Examples of the invention are shown below. A structural formula and physical properties are demonstrated in table 1. In the table, upper side of elemental analysis is a calculated value and lower side thereof is a theoretical value.

<Example 1> a) To 15 ml of N,N-dimethylformamide solution of 1.2 g (3.70 mmol) of 5-(2-aminoethyl)-3,4-bis(4-methoxyphenyl)-isoxazole and 1.07 g (3.61 mmol) of α-ethoxycarbonyl-3,5-dimethoxy-4-hydroxycinnamic acid were added 670 mg (4.38 mmol) of 1-hydroxybenzotriazole and 900 mg (4.36 mmol) of N,N'-dicyclohexylcarbodiimide, and the resultant mixture was stirred at room temperature for 42 hours.

A 50 ml of ethyl acetate was added to the mixture, and the formed precipitate was removed by filtration. The filtrate was washed with water, dried over anhydrous magnesium sulfate and concentrated under reduced pressure. The residue was purified by silica gel column chromatography (hexane:ethyl acetate=1:1) to give 1.1 g (yield 50.6%) of a compound 1.

b) Synthesis of 5-(2-aminoethyl)-3,4-bis(4-methoxyphenyl)-isoxazole

To 430 ml of tert-butanol were added 128 g of deoxyanisoine, 67.3 g of potassium tert-butoxide and 116 g of methyl 3-methoxyacrylate, and the mixture was stirred at 70° C. for 3 hours. To the resulting mixture was added n-hexane, and the mixture was allowed to stand at room temperature. A formed precipitate was filtered and dissolved by adding 1,000 ml of ethyl acetate and 300 ml of 3N-sulfuric acid. An organic layer was separated, washed with 3N-sulfuric acid and saturated brine and dried over anhydrous magnesium sulfate. The organic layer was concentrated under reduced pressure to give 153 g (yield 90%) of methyl 4,5-bis(4-methoxyphenyl)-5-oxo-3-pentenoate as an oil.

A mixture of 24.5 g of methyl 4,5-bis(4-methoxyphenyl)-5-oxo-3-pentenoate and 51.5 g of hydroxylamine hydrochloride in a mixture of 650 ml of methanol and 72 ml of water was heated under reflux for 23 hours. During this procedure, 0.9 equivalent of sodium bicarbonate was added portionwise to the reaction mixture as the reaction progressed. After completion of the reaction, methanol was evaporated under reduced pressure. Water and ethyl acetate were added to the residue for dissolution thereof, the organic layer was separated, washed with saturated brine and dried over anhydrous magnesium sulfate. The organic layer was then concentrated under reduced pressure and the residue was separated and purified by silica gel column chromatography (ethyl acetate:hexane=1:1) to give 23 g (yield 90%) of methyl 5-hydroxyimino-4,5-bis(4-methoxyphenyl)-3-pentenoate as an oil.

A 3.7 g of methyl 5-hydroxyimino-4,5-bis(4-methoxyphenyl)-3-pentenoate in 40 ml of acetic acid was stirred at 60° C. for 24 hours while blowing air into the mixture in the presence of 0.4 g of cobalt acetate tetrahydrate. After completion of the reaction, 3N sulfuric acid was added to the solution, and the resulting mixture was extracted with ethyl acetate. The organic layer was washed with saturated aqueous potassium carbonate solution and saturated brine in that order, and dried over anhydrous magnesium sulfate. The organic layer was then concentrated under reduced pressure and the residue was separated and purified by silica gel column chromatography (ethyl acetate:hexane=1:1) to give 3.3 g (yield 90%) of 5-methoxycarbonylmethyl-3,4-bis(4-methoxyphenyl)isoxazole.

A 5.9 g of sodium borohydride was added to a suspension of 5 g of 5-methoxycarbonylmethyl-3,4-bis(4-methoxyphenyl)isoxazole in 20 ml of methanol, and the resulting mixture was stirred for 1 hour with ice cooling. The reaction mixture was made acidic by portionwise addition of 1N hydrochloric acid and then extracted with 80 ml of ethyl acetate. The organic layer was washed with 20 ml of 1N hydrochloric acid and 20 ml of water in that order, subsequently dried over anhydrous magnesium sulfate and concentrated under reduced pressure to give 4.5 g (yield 98%) of 5-(2-hydroxyethyl)-3,4-bis(4-methoxyphenyl)isoxazole.

Diethyl azodicarboxylate (0.62 ml) was added to a solution of 1.3 g of 5-(2-hydroxyethyl)-3,4-bis(4-methoxyphenyl)isoxazole, 1.1 g of triphenylphosphine and 600 mg of phthalimide in 15 ml of tetrahydrofuran with ice cooling under a nitrogen atmosphere. The mixture was stirred for 20.5 hours. Diethyl ether (150 ml) was added to the reaction mixture for extraction. The organic layer was washed with 30 ml of water, dried over anhydrous magnesium sulfate, and concentrated under reduced pressure. The residue was purified by silica gel column chromatography (hexane:ethyl acetate=2:1) to give 1.5 g of the corresponding phthalimide compound.

This phthalimide compound was suspended in 15 ml of ethanol. A 165 mg of hydrazine hydrate was added to the suspension, and the mixture was stirred at room temperature for 40.5 hours. A crystalline precipitate was filtered off and washed with 10 ml of ethanol. The mother liquor and the washings were combined and concentrated under reduced pressure. The residue was purified by silica gel column chromatography (20% methanol/chloroform) to give 600 mg (yield 46%) of 5-(2-aminoethyl)-3,4-bis(4-methoxyphenyl)isoxazole.

c) Synthesis of α-ethoxycarbonyl-3,5-dimethoxy-4-hydroxycinnamic acid

A 1 g (3.70 mmol) of 3,5-dimethoxy-4-(β-methoxyethoxy)methoxybenzaldehyde and 815 mg (3.70 mmol) of β-methoxyethoxymethyl-ethylmalonate was dissolved in 20 ml of benzene. A 0.2 ml (2.02 mmol) of peperidine was added to the solorion, and the mixture was stirred at 140° C. for about 5 hours.

The mixture was evaporated under reduced pressure. The residue was purified by silica gel column chlomatography (hexane:ethyl acetate=1:0.5–1). The oil product thus obtained was dissolved in 20 ml of tetrahydrofuran. Five drops of conc. hydrochloric acid were added to the solution, and the mixture was stirred at room temperature for 48 hours. To the reaction mixture was added 30 ml of ethyl acetate, and the organic solution was washed with water, dried over anhydrous magnesium sulfate to give 830 mg (yield 75.7%) of desired α-ethoxy-3,5-dimethoxy-4-hydroxycinnamic acid.

(Example 2)

a) A compound 2 was obtained using α-cyano-3,5-dimethoxy-4-hydroxycinnamic acid in place of α-ethoxycarbonyl-3,5-dimethoxy-4-hydroxycinnamic acid according to example 1a).

b) Synthesis of a-cyano-3,5-dimethoxy-4-hydroxycinnamic acid

To a solution of 2 g (11.0 mmol) of syringaldehyde and 1.2 ml (11.3 mmol) of ethyl cyanoacetate in 30 ml of ethanol was added 2 ml of piperidine, and the mixture was stirred at room temperature for 16 hours. The solution was evaporated under reduced pressure, subsequently the residue was acidified by adding 1N hydrochloric acid and extracted with 200 ml of ethyl acetate. The organic layer was washed with water, and concentrated under reduced pressure. A formed precipitate was washed with ethanol, and then dissolved in a mixed solvent of tetrahydrofuran and methanol (30 ml, 20 ml). To the solution was added potassium hydroxide solution (3.0 g/30 ml), and the mixture was stirred at room temperature for 1.5 hours. A 100 ml of water and 50 ml of ethyl acetate was added to the solution for separation of each layer. An aqueous layer was acidified with conc. hydrochloric acid, and a formed precipitate was filtrated to give 1.4 g (yield 51.1%) of objective α-cyano-3,5-dimethoxy-4-hydroxycinnamic acid.

(Example 3)

a) To a solution of 500 mg (1.54 mmol) of 5-(2-aminoethyl)-3,4-bis(4-methoxyphenyl)isoxazole and 550 mg (1.54 mmol) of α-methoxymethyl-3,5-dimethoxy-4-(β-methoxyethoxy)methoxy-cinnamic acid in 25 ml of dry methylene chloride were added 22 mg (0.18 mmol) of 4-dimethylaminopyridine and 380 mg (1.84 mmol) of N,N'-dicyclohexylcarbodiimide while ice cooling, and the resultant mixture was stirred at room temperature for 40 hours. The mixture was concentrated under reduced pressure. To the residue was added 30 ml of ethyl acetate to filter off a precipitate formed. The filtrate was concentrated under reduced pressure. The residue was purified by silica gel column chromatography (hexane:ethyl acetate=1:2) to give an oil, which was dissolved in 20 ml of methanol. To the solution was added a small amount of p-toluenesulfonic acid monohydrate, and the mixture was stirred at room temperature for 17 hours. The solution was evaporated under reduced pressure. The residue was purified by silica gel column chromatography (hexane:ethyl acetate=1:2) to give 421 mg (yield 47.6%) of a compound 3.

b) Synthesis of a-methoxymethyl-3,5-dimethoxy-4-(β-methoxyethoxy)methoxycinnamic acid A solution of 2.6 g (22.0 mmol) of methyl 3-methoxypropionate in 5 ml of tetrahydrofuran was added to a solution of 666 mg of sodium hydride in 15 ml of tetrahydrofuran solution with ice cooling, subsequently to the resulting solution was added a solution of 3 g (1.1 mmol) of 3,5-dimethoxy-4-(β-methoxyethoxy)methoxybenzaldehyde in 10 ml of tetrahydrofuran. The mixture was stirred at room temperature for 17 hours. The mixture was extracted with 60 ml of ethyl acetate after adding ice to the solution. The organic layer was washed with water and dried over anhydrous magnesium sulfate, and concentrated under reduced pressure. The oily product thus obtained was dissolved in 20 ml of tetrahydrofuran. An aqueous potassium hydroxide solution (740 mg/5 ml) was added to the solution. The mixture was stirred at room temperature for 21 hours. The solution was evaporated under reduced pressure. A 40 ml of water was added to the residue, and the aqueous solution was washed with 30 ml of ethyl acetate. The aqueous layer was neutralized with acetic acid and extracted with 60 ml of methylene chloride. The organic layer was dried over anhydrous magnesium sulfate, and evaporated under reduced pressure to give 2.5 g (yield 63.2%) of a desired α-methoxymethyl-3,5-dimethoxy-4-(β-methoxyethoxy)-methoxycinnamic acid.

(Example 4)

A compound 4 was obtained in the same way as example 3 by using ethyl valerate in place of methyl 3-methoxypropionate.

(Examples 5–12)

Compounds 5–12 were obtained in the same way as in example 2

(Example 13)

a) A compound 13 was obtained in the same manner as in example 1 a) using 5-(3-aminopropyl)-3,4-bis(4-methoxyphenyl)isoxazole and a α-N,N-dimethylcarbamoyl-3,5-dimethoxy-4-hydroxycinnamic acid.

b) Synthesis of 5-(3-aminopropyl)-3,4-bis(4-methoxyphenyl)isoxazole

A 18 g of deoxyanisoin ketoxime was dissolved in 180 ml of tetrahydrofuran. To the solution was added dropwise 94 ml of n-butyllithium (1.6M) at 0° C. under nitrogen atmosphere. After 30 minutes, a 8.2 g of succinic anhydride in 100 ml of tetrahydrofuran solution was added dropwise to the solution. The mixture was stirred for 3 hours, acidified with 1N-hydrochloric acid and extracted with 100 ml of ethyl acetate. The ethyl acetate layer was extracted twice with 50 ml 1N aqueous sodium hydroxide solution. The aqueous layers were acidified with conc. hydrochloric acid and extracted with 100 ml of ethyl acetate. The residue was dissolved in 80 ml of methanol to which several drops of conc. sulfuric acid were added. The solution was stirred at room temperature for 12 hours and then evaporated under reduced pressure. The residue was dissolved in 100 ml of ethyl acetate. The ethyl acetate solution was washed with 50 ml of saturated sodium bicarbonate and 50 ml of saturated brine, dried over anhydrous magnesium sulfate and concentrated under reduced pressure. The residue was purified by silica gel column chromatography (chloroform). A 3,4-bis(4-methoxyphenyl)isoxazole-5-propionic acid thus obtained was suspended in 1,000 ml of methanol. To the suspension was added 0.5 ml of conc. sulfuric acid, and the mixture was stirred at room temperature for 24 hours. A crystalline precipitated was filtered to give 13.5 g (yield 52.0%) of methyl 3,4-bis(4-methoxyphenyl)isoxazole-5-propionate. A 2.8 (yield 23.4%) of objective 5-(3-aminopropyl)-3,4-bis(4-methoxyphenyl)isoxazole was obtained in the same manner as in example 1b.

c) Synthesis of a -N,N-dimethylcarbamoyl-3,5-dimethoxy-4-hydroxycinnamic acid

A 8.1 g (44.5 mmol) of syringaldehyde, 7.2 g (44.4 mmol) of ethyl a-dimethylcarbamoylacetate and 6.6 ml (66.7 mmol) of piperidine in 150 ml of ethanol solution was stirred at 110° C. for about 12 hours. The mixture was concentrated under reduced pressure and purified by silica gel column chromatography (methanol/chloroform=2–4%). An oily product thus obtained was dissolved in 50 ml of tetrahydrofuran. To the solution was added an aqueous potassium hydroxide solution (4.3 g/10 ml), and the solution was stirred at room temperature for 15 hours. A 50 ml of ethyl acetate was added to the solution. The mixture was extracted with 100 ml of water. The aqueous layer was acidified with conc. hydrochloric acid and extracted with 120 ml of methylene chloride. The organic layer was dried over anhydrous magnesium sulfate and evaporated under reduced pressure to give 4.6 g (yield 35%) of objective α-dimethylcarbamoyl-3,5-dimethoxy-4-hydroxycinnamic acid.

(Example 14)

A 200 mg (0.33 mmol) of compound 1 was dissolved in a mixture of tetrahydrofuran and methanol (5 ml, 5 ml). An aqueous potassium hydroxide solution (65 mg/3 ml) was added to the solution. The resulting mixture was stirred at room temperature for 67 hours. A 50 ml of ethyl acetate was added to the solution, and the mixture was extracted with 30 ml of 1N sodium hydroxide solution. The aqueous layer was acidified with conc. hydrochloric acid and extracted with 60 ml of methylene chloride. The organic layer was dried over anhydrous magnesium sulfate and concentrated to dryness under reduced pressure to give 106 mg (yield 55.9%) of a compound 14.

(Example 15)

To a 10 ml of tetrahydrofuran solution of 205 mg (0.36 mmol) of the compound 14 and 75 mg (0.39 mmol) of p-toluenesulfonyl chloride was added 0.05 ml (0.36 mmol) of triethylamine with ice cooling. After stirring the solution for two hours, gaseous ammonia was blowed into the solution for 30 minutes. The mixture was stirred at room temperature for 12 hours, evaporated under reduced pressure, purified by silica gel column chromatography (hexane:ethyl acetate=1:2) and recrystallized from hexane-ethanol to give 23 mg (yield 11%) of compound 15.

(Example 16)

a) A compound 16 was Obtained in the same manner as in example 1 using a-methoxycarbonylmethyl-3,5-dimethoxy-4-hydroxycinnamic acid.

b) Synthesis of a-methoxycarbonylmethyl-3,5-dimethoxy-4-hydroxycinnamic acid

A 3.6 g of syringaldehyde and 5 ml of diethyl succinate were dissolved in 60 ml of tetrahydrofuran. To the solution was added 4.9 g of potassium t-butoxide, and the mixture was heated under reflux for 24 hours. The mixture was poured into ice water. The aqueous solution was acidified with 6N hydrochloric acid and extracted with 100 ml of ethyl acetate. An organic layer was washed with saturated brine, dried over anhydrous magnesium sulfate and evaporated under reduced pressure. The residue was purified by silica gel column chromatography (ethyl acetate) to give 3 g (yield 48%) of ethyl α-carboxymethyl-3,5-dimethoxy-4-hydroxycinnamate. The product was dissolved in 20 ml of N,N-dimethylformamide. To the solution was added 2.1 g of N,N'-dicyclohexylcarbodiimide, and the mixture was stirred at room temperature for 30 minutes. To the mixture was added methanol to filter off an insoluble material, which was washed with methanol and dried to give 2 g (yield 80 %) of the corresponding acid anhydride compound.

The acid anhydride compound was suspended in 10 ml of methanol. A 0.2 ml of conc. sulfuric acid was added to the suspension, and the mixture was stirred at room temperature for 24 hours. The reaction mixture was evaporated under reduced pressure, extracted with 50 ml of ethyl acetate, washed with saturated brine and dried over anhydrous magnesium sulfate. The solution was concentrated to dryness under reduced pressure to give 2 g (yield 90%) of objective α-methoxycarbonylmethyl-3,5-dimethoxy-4-hydroxycinnamic acid.

(Example 17)

a) A compound 17 was obtained in the same manner as in example 1 a) using α-dimethylcarbamoylmethyl-3,5-dimethoxy-4-hydroxycinnamic acid.

b) Synthesis of α-dimethylcarbamoylmethyl-3,5-dimethoxy-4-hydroxycinnamic acid

A 1 g of α-[(3,5-dimethoxy-4-hydroxy)benzylidene]succinic anhydride prepared in the same manner as in example 16b) was dissolved in 10 ml of tetrahydrofuran. A gaseous dimethylamine was blowed into the solution with ice cooling. After 30 minutes, an insoluble material was filtered and washed with tetrahydrofuran to give 0.9 g (yield 70%) of desired α-dimethylcarbamoylmethyl-3,5-dimethoxy-4-hydroxycinnamic acid.

(Example 18)

a) A compound 18 was obtained in the same manner as in example 1 using α-N-acetylamino-3,5-dimethoxy-4-hydroxycinnamic acid.

b) Synthesis of a—N-acetylamino-3,5-dimethoxy-4-hydroxycinnamic acid

A 1.8 g (9.88 mmol) of syringaldehyde, 1.4 g (12.0 mmol) of N-acetylglycine, 1 g (12.2 mmol) of sodium acetate and 5 ml of acetic anhydride were stirred at 120° C. for 6 hours. A precipitate was washed with water and ethanol in this order and dried under reduced pressure. To the product was added 80 ml of 0.1N hydrochloric acid, and the mixture was stirred at 90° C. for 1 hour. A crystal formed was washed with water and acetone in this order to give 880 mg (yield 31.7%) of objective αacetylamino-3,5-dimethoxy-4-hydroxycinnamic acid.

(Example 19)

A compound 19 was obtained in the same manner as in example 18.

(Example 20)

a) A mixture of 200 mg (0.62 mmol) of 5-cyanomethyl-3,4-bis(4-methoxyphenyl)isoxazole, 170 mg (0.63 mmol) of 3,5-dimethoxy-4-(β-methoxyethoxy)methoxybenzaldehyde, 2 ml of piperidine and 10 ml of ethanol was stirred at 120° C. for 17 hours. The mixture was extracted with 80 ml of ethyl acetate. The ethyl acetate layer was washed with water, dried over anhydrous magnesium sulfate, concentrated under reduced pressure and purified by silica gel column chromatography (hexane:ethyl acetate=2–1:1). An oily product thus obtained was dissolved in 20 ml of methanol. A small amount of p-toluenesulfonic acid monohydrate was added to the solution. The mixture was stirred for 3 hours, evaporated under reduced pressure. The residue was recrystallized from ethanol to give a 124 mg (yield 41.3%) of compound 20.

b) Synthesis of 5-cyanomethyl-3,4-bis(4-methoxyphenyl)isoxazole

A 10 g of deoxyanisoine ketoxime was dissolved in 100 ml of tetrahydrofuran. To the solution 49 ml of 1.6 mole n-butyllithium was added dropwise at a temperature equal to or lower than 10° C. under nitrogen atmosphere. After 1 hour, a 7.8 g chloroacetic anhydride in 40 ml of tetrahydrofuran solution was added dropwise to the mixture. The resulting mixture was stirred for 1.5 hours. A 30 ml of conc. sulfuric acid and the mixture was further stirred at room temperature for 11.5 hours. A 200 ml of ethyl acetate was added to the mixture, and the mixture was washed with 50 ml of water for 3 times, dried over anhydrous magnesium sulfate and concentrated under reduced pressure. The residue was purified by silica gel column chromatography (hexane:ethyl acetate=4:1) to give 3.8 g (yield 32%) of 5-chloromethyl-3,4-bis(4-methoxyphenyl)isoxazole.

A 500 mg of 5-chloromethyl-3,4-bis(4-methoxyphenyl)isoxazole was dissolved in a mixed solvent of dimethylsulfoxide (3 ml) and water (1 ml). To the solution, 122 mg of potassium cyanide was added, and the mixture was stirred at room temperature for 18 hours. A 80 ml of ethyl acetate was added to the mixture. The resulting mixture was washed with water, dried over anhydrous magnesium sulfate and concentrated under reduced pressure. The residue was purified by silica gel column chromatography (hexane:ethyl acetate=4:1) to give 210 mg (yield 43.1%) of a desired 5-cyanomethyl-3,4-bis(4-methoxyphenyl)isoxazole.

(Example 21)

A mixture of 10 g of methyl 3,4-bis(4-methoxy-phenyl)isoxazole-5-acetate, 4.4 g of vaniline, 25 ml of piperidine and 40 ml of ethanol was heated under reflux for 19 hours, allowed to stand for cooling the solution and concentrated under reduced pressure. A 250 ml of ethyl acetate was added to the residue. The resulting solution was washed with water, 1N hydrochloric acid in this order, dried over anhydrous magnesium sulfate and concentrated under reduced pressure. The residue was purified by silica gel column chromatography (hexane:ethyl acetate=2:1). The product thus obtained was dissolved in 10 ml of methanol. To the solution, an aqueous potassium hydroxide solution (1.1 g, 1.0 ml) was added, The mixture was stirred at room temperature for 11 hours, concentrated under reduced pressure and separated by adding 30 ml of ethyl acetate and 70 ml of water. The aqueous layer was acidified with conc. hydrochloride, extracted with methylene chloride, dried over anhydrous magnesium sulfate and concentrated to dryness under reduced pressure to give 5.3 g (yield 39.6%) of compound 21.

(Example 22)

a) A compound 22 was obtained in the same manner as in example 1a) using 5-[2-(N-methoxycarbonylmethyl)aminoethyl]-3,4-bis-(4-methoxyphenyl)isoxazole.

b) Synthesis of 5-[2-(N-methoxycarbonylmethyl)aminoethyl]-3,4-bis-(4-methoxyphenyl)isoxazole To a benzene (20 ml) solution of 3.1 g of 5-(2-aminoethyl)-3,4-bis-(4-methoxyphenyl)isoxazole was added 0.44 ml of methyl bromoacetate, and the mixture was heated under reflux for 4 hours, and then concentrated under reduced pressure. The residue was purified by silica gel column chromatography (hexane:ethyl acetate=1:1) to give 2 g (yield 52.7%) of 5-[2-(N-methoxycarbonylmethyl)-aminoethyl]-3,4-bis-(4-methoxyphenyl)isoxazole.

(Example 23)

A compound 23 was obtained in the same manner as example 14 using compound 22.

(Example 24)

a) A compound 24 was obtained in the same manner as in example 1a) using γ-cyano-6-(3,5-dimethoxy-4-hydroxy)phenyl-2,4-pentadienic acid.

b) Synthesis of γ-cyano-6-(3,5-dimethoxy-4-hydroxy)phenyl-2,4-pentadienic acid

A 4.0 ml of n-butyllithium (1.6M) was added to a tetrahydrofuran (20 ml) solution of diisopropylamine (0.9 ml) at −70° C. under nitrogen atmosphere. After 15 minutes, to the solution was added a tetrahydrofuran (8 ml) solution of 1.24 g of 3,5-dimethoxy-4-hydroxycinnamonitrile at −60° C. or less, and the solution was stirred for 1 hour. A 0.7 ml of ethyl formate was added to the solution, and the mixture was further stirred for 1 hour. A 1N hydrochloric acid was added to the mixture and a temperature of the mixture was elevated to room temperature. The mixture was extracted with 250 ml of ethyl acetate, dried over anhydrous magnesium sulfate and concentrated under reduced pressure. A crystal formed was washed with ethanol to give 430 mg (yield 43.6%) of α-formyl-3,5-dimethoxy-4-hydroxycinnamonitrile. The compound thus obtained was dissolved in 20 ml of tetrahydrofuran- To the solution 3.2 g of carbethoxymethylenetriphenylphosphorane was added. The mixture was stirred at room temperature for 32 hours, and concentrated under reduced pressure. A 80 ml of ethyl ether was added to the residue. The solution was washed with water and 1N hydrochloric acid in this order, dried over anhydrous magnesium sulfate and concentrated under reduced pressure. A crystal formed was washed with ethanol to give 320 mg (yield 57.3%) of γ-cyano-6-(3,5-dimethoxy-4-hydroxy)phenyl-2,4-pentadienic acid ethyl ester, which was dissolved in a mixed solvent of tetrahydrofuran (8 ml) and methanol (10 ml). To the solution, an aqueous potassium hydroxide solution (140 mg/5 ml) was added. The mixture was stirred at room temperature for 48 hours, concentrated under reduced pressure. A 70 ml of water was added to the residue. The aqueous solution was washed with ethyl acetate and acidified with conc. hydrochloride. The aqueous layer was extracted with 200 ml of ethyl acetate, dried over anhydrous magnesium sulfate and concentrated to dryness under reduced pressure to give 190 mg (yield 65.1%) of a desired γ-cyano-β-(3,5-dimethoxy-4-hydroxy)phenyl-2,4-pentadienic acid.

(Example 25)

A 150 mg of the compound 2 was dissolved in 10 ml of methylene chloride. To the solution were added 0.03 ml of pyridine and 0.03 ml of ethyl chloroformate with ice cooling, and the mixture was stirred for 5 minutes. The reaction mixture was diluted with 30 ml of methylene chloride, washed with water, dried over anhydrous magnesium sulfate and evaporated under reduced pressure. The residue was recrystallized from toluene to give 117 mg (yield 69.0%) of a compound 25.

(Examples 26–29)

Compounds 26–29 were obtained in the same manner as example 25.

(Example 30)

A 300 mg of compound 8 was dissolved in 3 ml of dimethylformamide. To the solution were added 95 mg of N-t-butoxycarbonylglycine, 90 mg of 1-hydroxybenzotriazole and 121 mg of N,N'-dicyclohexylcarbodiimide, and the reaction mixture was stirred at room temperature for 48 hours. To the mixture was added 50 ml of ethyl acetate to filtered off a precipitate. An organic layer was washed with water, dried over anhydrous magnesium sulfate and evaporated under reduced pressure. The residue was purified by silica gel column chromatography (hexane:ethyl acetate= 1:10) and recrystallized from ethanol to give 50 mg (yield 13%) of a compound 30.

(Example 31)

A 40 mg of the compound 30 was dissolved in 5 ml of ethyl acetate. To the solution was added 0.5 ml of 4N hydrochloric acid/ethyl acetate, and the mixture was stirred at room temperature for 15 hours. A precipitate formed was filtered to give 20 mg (yield 54.6%) of a compound 31.

The results are shown in Table 1.

TABLE 1

| No. | Structure and Chemical Formula | | M.P. (°C.) | Elemental Analysis (%) | | |
|---|---|---|---|---|---|---|
| | | | | (C | H | N) |
| 1 | 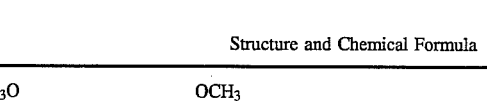 | $C_{33}H_{34}N_2O_9 \cdot H_2O$ | 109–110 | 63.43 | 5.60 | 4.47 |
| | | | | 63.86 | 5.85 | 4.51 |

TABLE 1-continued

| | Structure | Formula | mp (°C) | C | H | N |
|---|---|---|---|---|---|---|
| 2 | (4-MeO-C6H4)2-isoxazole-CH2CH2-NH-CO-C(CN)=CH-(3,5-diMeO-4-OH-C6H2); ¼H2O | C31H29N3O7·¼H2O | 139–140 | 66.45<br>66.48 | 5.35<br>5.31 | 7.46<br>7.50 |
| 3 | (4-MeO-C6H4)2-isoxazole-CH2CH2-NH-CO-C(CH2OCH3)=CH-(3,5-diMeO-4-OH-C6H2); ½H2O | C32H34N2O8·½H2O | amorphous | 65.49<br>65.85 | 6.40<br>6.04 | 4.45<br>4.80 |
| 4 | (4-MeO-C6H4)2-isoxazole-CH2CH2-NH-CO-C(CH2CH3)=CH-(3,5-diMeO-4-OH-C6H2); H2O | C33H36N2O7·H2O | amorphous | 67.30<br>67.10 | 6.26<br>6.48 | 4.68<br>4.74 |
| 5 | (4-MeO-C6H4)2-isoxazole-CH2CH2-NH-CO-C(4-OMe-C6H4)=CH-(3,5-diMeO-4-OH-C6H2); ⅓H2O | C37H36N2O8·⅓H2O | amorphous | 69.08<br>69.15 | 6.00<br>5.75 | 4.64<br>4.36 |

5,478,856

TABLE 1-continued

| | | | | |
|---|---|---|---|---|
| 6 | [structure] | $C_{35}H_{33}N_3O_7 \cdot H_2O$ | amorphous | 67.43 5.69 6.69 / 67.19 5.64 6.72 |
| 7 | [structure] | $C_{34}H_{32}N_2O_7S \cdot H_2O$ | amorphous | 64.52 5.36 4.48 / 64.75 5.43 4.44 |
| 8 | [structure] | $C_{33}H_{35}N_3O_8 \cdot H_2O$ | amorphous | 64.32 6.17 6.34 / 63.96 6.02 6.78 |
| 9 | [structure] | $C_{39}H_{47}N_3O_6$ | 203.5–204 | 71.43 7.47 6.31 / 71.64 7.25 6.43 |
| 10 | [structure] | $C_{31}H_{31}N_3O_7 \cdot H_2O$ | 148.5–150 | 64.65 5.59 7.20 / 64.69 5.78 7.30 |

TABLE 1-continued

| No. | Structure | Formula | Form | Analysis |
|---|---|---|---|---|
| 11 | (structure) | $C_{33}H_{31}N_3O_7 \cdot 3/2 H_2O$ | amorphous | 65.00 5.35 6.61 / 65.12 5.63 6.90 |
| 12 | (structure) | $C_{35}H_{37}N_3O_8 \cdot 2H_2O$ | amorphous | 63.57 5.81 6.21 / 63.33 6.23 6.36 |
| 13 | (structure) | $C_{34}H_{37}N_3O_8 \cdot 1/2 H_2O$ | amorphous | 65.14 6.27 6.69 / 65.37 6.13 6.73 |
| 14 | (structure) | $C_{31}H_{30}N_2O_9$ | amorphous | 63.79 5.72 4.62 / 63.80 5.35 4.80 |
| 15 | (structure) | $C_{31}H_{31}N_3O_8 \cdot 1/2 H_2O$ | 174.5–175.5 | 63.93 5.56 7.09 / 63.91 5.54 7.21 |

TABLE 1-continued

| # | Structure | Formula | Form/mp | Analysis |
|---|---|---|---|---|
| 16 | (structure: 3,4-bis(4-methoxyphenyl)isoxazole with CH₂CH₂NH-CO-C(=CH-Ar)-CH₂-CO-OCH₃ where Ar = 4-hydroxy-3,5-dimethoxyphenyl) | $C_{33}H_{34}N_2O_9 \cdot 1/2 H_2O$ | amorphous | 64.75 5.88 4.51 / 64.79 5.76 4.58 |
| 17 | (structure: 3,4-bis(4-methoxyphenyl)isoxazole with CH₂CH₂NH-CO-C(=CH-Ar)-CH₂-CO-N(CH₃)₂) | $C_{34}H_{37}N_3O_8 \cdot 1/2 H_2O$ | amorphous | 64.92 6.00 6.63 / 65.36 6.13 6.72 |
| 18 | (structure: 3,4-bis(4-methoxyphenyl)isoxazole with CH₂CH₂NH-CO-C(=CH-Ar)-NH-COCH₃) | $C_{32}H_{33}N_3O_8$ | amorphous | 66.82 5.64 7.37 / 65.40 5.66 7.15 |
| 19 | (structure: 3,4-bis(4-methoxyphenyl)isoxazole with CH₂CH₂NH-CO-C(=CH-Ar)-NH-CO-Ph) | $C_{37}H_{35}N_3O_8 \cdot H_2O$ | amorphous | 66.26 5.51 6.12 / 66.55 5.58 6.29 |
| 20 | (structure: 3,4-bis(4-methoxyphenyl)isoxazole with C(CN)=CH-Ar, Ar = 4-hydroxy-3,5-dimethoxyphenyl) | $C_{28}H_{24}N_2O_6 \cdot H_2O$ | 95–97 | 66.81 5.02 5.32 / 66.92 5.22 5.57 |

TABLE 1-continued

| | Structure | Formula | mp/form | Analysis |
|---|---|---|---|---|
| 21 | | $C_{27}H_{23}NO_7 \cdot 3/4H_2O$ | amorphous | 66.39 5.30 2.76 / 66.59 5.07 2.88 |
| 22 | | $C_{35}H_{36}N_2O_9$ | amorphous | 67.03 5.96 4.43 / 66.80 5.77 4.45 |
| 23 | | $C_{34}H_{34}N_2O_9 \cdot 1/2H_2O$ | amorphous | 65.43 5.94 4.71 / 65.47 5.65 4.49 |
| 24 | | $C_{34}H_{34}N_2O_9 \cdot 1/2H_2O$ | amorphous | 65.43 5.94 4.71 / 65.47 5.65 4.49 |
| 25 | | $C_{34}H_{33}N_3O_9$ | 176–176.5 | 65.17 5.38 6.67 / 65.06 5.30 6.69 |

TABLE 1-continued

| No. | Structure | Formula | Form | Analysis |
|---|---|---|---|---|
| 26 | (structure shown) | C₃₈H₄₁N₃O₁₀ 1/2H₂O | amorphous | 64.30 6.13 5.54 / 64.39 5.97 5.92 |
| 27 | (structure shown) | C₃₈H₄₀N₂O₁₁ | amorphous | 64.97 5.75 3.99 / 65.13 5.75 3.99 |
| 28 | (structure shown) | C₃₅H₃₇N₃O₉ 3/2H₂O | amorphous | 62.38 5.68 6.16 / 62.68 6.01 6.26 |
| 29 | (structure shown) | C₃₇H₄₄N₃O₁₁P H₂O | amorphous | 58.84 6.10 5.50 / 58.81 6.13 5.56 |
| 30 | (structure shown) | C₄₀H₄₆N₄O₁₁ 5/2H₂O | 64–65 | 59.59 6.14 7.00 / 59.77 6.39 6.97 |

TABLE 1-continued

| 31 | [structure: bis(4-methoxyphenyl) isoxazoline with (CH₃)₂N-C(=O) and CH₂CH₂-NH-C(=O)-CH=C linked to 3,5-dimethoxy-4-(OCOCH₂NH₂·HCl·H₂O)phenyl] | $C_{35}H_{38}N_4O_9 \cdot HCl \cdot H_2O$ | amorphous | 58.84 5.70 7.78 |
|---|---|---|---|---|
|    |                                                                                                                                                |                                            |           | 58.94 5.79 7.86 |

| No. | ¹H-NMR(solvent) |
|---|---|
| 1 | (CDCl3)<br>1.29(t, 3H), 2.99–3.07(m, 2H), 3.69–3.78(m, 2H), 3.80(s, 3H), 3.83(s, 3H), 3.83(s, 3H), 4.22–4.30(q, 2H), 5.77 (s, 1H), 6.09–6.13(m, 1H), 6.81–6.94(m, 6H), 7.04–7.08(m, 2H), 7.33–7.36(m, 2H), 7.62(s, 1H) |
| 2 | (DMSO-d6)<br>2.97(m, 2H), 3.48–3.53(m, 2H), 3.72(s, 3H), 3.50(s, 3H), 3.80(s, 6H), 6.91–6.95(m, 4H), 7.13–7.16 (m, 2H), 7.28–7.35(m, 4H), 7.97(s, 1H), 8.40–8.43(m, 1H) |
| 3 | (CDCl3)<br>3.03–3.08(m, 2H), 3.42(s, 3H), 3.72–3.77(m, 2H), 3.80(s, 3H), 3.81(s, 3H), 3.89(s, 6H), 4.24(s, 2H), 5.65(s, 1H) 6.63)(s, 2H), 6.81–6.93)(m, 4H), 7.06–7.13(m, 3H), 7.35–7.41(m, 2H), 7.66(s, 1H) |
| 4 | (CDCl3)<br>0.95(t, 3H), 1.53(m, 2H), 2.48(m, 2H), 3.06(m, 2H), 3.73(m, 2H) 3.79(s, 3H), 3.81(s, 3H), 3.87(s, 6H), 5.62(s, 1H) 6.20(m, 1H), 6.54(s, 2H), 6.81–7.38(m, 8H) |
| 5 | (CDCl3)<br>2.99(t, 2H), 3.53–3.83(m, 17H), 5.76(br, 1H), 6.27(s, 2H) 6.82–7.04(m, 8H), 7.14(d, 2H), 7.36(d, 2H), 7.69(s, 1H) |
| 6 | (CDCl3)<br>3.00(m, 2H), 3.61(s, 6H), 3.69–3.87(m, 8H), 6.25(s, 2H) 6.80–7.66(m, 11H), 7.84(s, 1H), 7.91(br, 1H), 8.69(m, 1H) |
| 7 | (CDCl3)<br>3.01(t, 2H), 3.66–3.71(m, 8H), 3.80(s, 3H), 3.81(s, 3H) 6.04(br, 1H), 6.37(s, 2H), 6.81–7.47(m, 11H), 7.84(s, 1H) |
| 8 | (DMSO-d6)<br>2.73(s, 3H), 2.94(m, 2H), 2.95(s, 3H), 3.46(m, 2H), 3.72(s, 6H), 3.75(s, 3H), 3.77(s, 3H), 6.72(s, 2H), 6.92–6.98 (m, 4H), 7.12–7.31(m, 6H), 7.97(m, 1H) |
| 9 | (CDCl3)<br>1.41(s, 9H), 2.73(s, 3H), 2.99–3.04(m, 5H), 3.55–3.79(m, 8H), 6.80–7.38(m, 11H), 7.56(s, 1H) |
| 10 | (DMSO-d6)<br>2.68(s, 3H), 2.85–2.99(m, 5H), 3.75(s, 3H), 3.76(s, 3H) 6.71–7.31(m, 12H), 7.91(br, 1H) |
| 11 | (CDCl3)<br>3.08(t, 2H), 3.73(q, 2H), 3.79(s, 6H), 3.95(s, 6H), 5.87(s, 1H) 6.33(t, 1H), 6.79(s, 2H), 6.81–7.37(m, 10H), 7.94(d, 1H) |
| 12 | (CDCl3)<br>3.01(q, 2H), 3.00(s, 3H), 3.14(s, 3H), 3.65(q, 2H), 3.79(s, 3H) 3.82(s, 3H), 3.91(s, 6H), 5.76(s, 1H), 6.50(q, 1H), 6.66(s, 2H) 6.80–7.38(m, 11H) |
| 13 | (DMSO-d6)<br>1.82–1.87(m, 2H), 2.71(s, 3H), 2.73(m, 2H), 2.94S, 3H), 3.20(m, 2H), 3.72, 3.73, 3.75(s × 3, 12H), 6.72(s, 2H), 6.91–6.98 (m, 4H), 7.12–7.18(m, 3H), 7.27–7.31(m, 2H), 7.83(m, 1H) |
| 14 | (DMSO-d6)<br>2.87–2.92(m, 2H), 3.50(m, 2H), 3.69(s, 6H), 3.75(s, 3H), 3.77(s, 3H), 6.86–6.99(m, 6H), 7.12–7.17(m, 2H), 7.21–7.32 (m, 2H), 7.43(s, 1H)8.58(m, 1H), 9.06(s, 1H) |
| 15 | (CDCl3)<br>2.91(t, 2H), 3.6(m, 2H), 3.7–3.9(m, 12H), 5.70(s, 1H), 6.0(br, 1H), 6.65(s, 2H), 6.84–7.35(m, 8H), 7.79(s, 1H) |
| 16 | (CDCl3)<br>3.07(t, 2H), 3.72(s, 3H), 3.73(t, 2H), 3.79(s, 3H), 3.81(s, 3H) 3.88(s, 6H), 5.67(s, 1H), 6.66(s, 2H), 6.88(d, 2H), 6.90(d, 2H) 7.10(d, 2H), 7.35(d, 2H), 7.38(d, 2H) |
| 17 | (CDCl3)<br>2.95(s, 3H), 2.96(s, 3H), 3.04(t, 2H), 3.51(s, 2H), 3.68(q, 2H) 3.80(s, 6H), 3.83(s, 6H), 5.65(s, 1H), 6.51(s, 2H), 6.81(d, 2H) 6.83(d, 2H), 7.11(d, 2H), 7.21(d, 1H), 7.38(d, 2H) |
| 18 | (CDCl3)<br>2.10(s, 3H), 3.12(t, 2H), 3.71(s, 3H), 3.78(s, 3H), 3.92(t, 2H) 3.94(s, 6H), 6.77–6.84(m, 5H), 7.38(d, 2H), 7.47(s, 2H) |
| 19 | (CDCl3)<br>3.00(t, 2H), 3.63(s, 6H), 3.67(q, 2H), 3.78(s, 6H), 5.69(s, 1H) 6.65(s, 2H), 6.78–7.93(m, 14H) |
| 20 | (CDCl3)<br>3.80(s, 3H), 3.85(s, 3H), 3.93(s, 6H), 5.97(s, 1H), 6.84(d, 2H) 6.97(d, 2H), 7.18–7.26(m, 4H), 7.39(d, 2H), 7.73(s, 1H) |
| 21 | (CDCl3)<br>3.66(s, 3H), 3.77(s, 3H), 3.81(s, 3H), 5.92(br, 1H), 6.53(s, 1H)6.73–7.06(m, 9H),<br>7.42(d, 2H), 8.04(s, 1H) |
| 22 | (CDCl3)<br>3.08(t, 2H), 3.71(s, 3H), 3.73(t, 2H), 3.77(s, 3H), 3.77(s, 3H) 3.95(s, 6H), 3.97(t, 2H), 5.70(s, 1H), 6.10(d, 1H), 6.68–7.46 (m, 13H), |
| 23 | (CDCl3)<br>3.08(t, 2H), 3.76(s, 3H), 3.77(s, 3H), 3.83(t, 2H), 3.90(d, 2H) 3.94(s, 6H), 6.06(d, 1H), 6.68–7.46(m, 13H) |
| 24 | (CDCl3)<br>3.04–3.09(m, 2H), 3.69–3.76(m, 2H), 3.80(s, 3H), 3.82(s, 3H) 3.96(s, 6H), 5.87(m, 1H), 5.97(s, 1H), 6.17(d, 1H), 6.82–6.95 (m, 4H), 7.09–7.40(m, 8H) |
| 25 | (CDCl3) |

TABLE 1-continued

|   | |
|---|---|
| | 1.40(t, 3H), 3.10–3.15(m, 2H), 3.72(s, 3H), 3.74–3.76(m, 2H) 3.80(s, 3H), 3.90(s, 6H), 4.29–4.37(q, 2H), 6.49–6.51(m, 1H) 6.80–6.90(m, 4H), 7.10–7.13(m, 2H), 7.21(s, 2H), 7.36–7.39(m, 2H), 8.12(s, 1H) |
| 26 | (CDCl3) |
| | 1.38(t, 3H), 2.99(q, 2H), 2.99(s, 3H), 3.13(s, 3H), 3.65(q, 2H) 3.79(s, 3H), 3.86(s, 3H), 3.91(s, 6H), 4.34(q, 2H), 6.56(q, 1H) 6.65(s, 2H), 6.81–7.38(m, 11H) |
| 27 | (CDCl3) |
| | 1.39(t, 3H), 3.08(t, 2H), 3.71(s, 3H), 3.73(t, 2H), 3.77(s, 3H) 3.77(s, 3H), 3.95(s, 6H), 3.97(t, 2H), 4.32(q, 2H), 6.12(d, 1H) 6.68–7.46(m, 13H) |
| 28 | (CDCl3) |
| | 2.34(s, 3H), 2.72(s, 3H), 2.96–3.03(m, 5H), 3.53–3.80(m, 8H), 6.67(s, 2H), 6.81–7.15(m, 7H), 7.37(d, 2H), 7.55 (s, 1H) |
| 29 | (CDCl3) |
| | 1.39(m, 6H), 2.72(s, 3H), 2.95–3.10(m, 5H), 3.56–3.83(m, 8H), 4.31(m, 4H), 6.66(s, 2H), 6.81–7.14(m, 7H), 7.37 (d, 2H), 7.52(s, 1H) |
| 30 | (CDCl3) |
| | 1.47(s, 9H), 2.71(s, 3H), 3.00–3.03(m, 5H), 3.53–3.83(m, 14H), 4.26(d, 2H), 5.05(br, 1H), 6.67(s, 2H), 6.81–7.15 (m, 7H), 7.37(d, 2H), 7.54(s, 1H) |
| 31 | (DMSO-d6) |
| | 2.78(s, 3H), 2.90–3.00(m, 5H), 3.43–3.53(m, 2H), 3.76(m, 12H), 4.19(s, 2H), 6.87(s, 2H), 6.92–7.31(m, 9H) 8.16(br, 1H) |

Dosage Form Examples

Several dosage form examples in which certain compounds of the invention are used are given below.

Dosage Form Example 1 Tablets

Tablets were prepared in the conventional manner according to the following formulation.

| | |
|---|---|
| Compound 1 | 100 mg |
| Lactose | 47 mg |
| Corn starch | 50 mg |
| Crystalline cellulose | 50 mg |
| Hydroxypropylcellulose | 15 mg |
| Talc | 2 mg |
| Magnesium stearate | 2 mg |
| Ethylcellulose | 30 mg |
| Unsaturated fatty acid glyceride | 2 mg |
| Titanium dioxide | 2 mg |
| Per one tablet | 300 mg |

Dosage Form Example 2 Granules

Granules were prepared in the conventional manner according to the following formulation.

| | |
|---|---|
| Compound 3 | 200 mg |
| Mannitol | 540 mg |
| Corn starch | 100 mg |
| Crystalline cellulose | 100 mg |
| Hydroxypropylcellulose | 50 mg |
| Talc | 10 mg |
| Per one wrapper | 1000 mg |

Dosage Form Example 3 Fine granules

Fine granules were prepared in the conventional manner according to the following formulation.

| | |
|---|---|
| Compound 6 | 200 mg |
| Mannitol | 520 mg |
| Corn starch | 100 mg |
| Crystalline cellulose | 100 mg |
| Hydroxypropylcellulose | 70 mg |
| Talc | 10 mg |
| Per one wrapper | 1000 mg |

Dosage Form Example 4 Capsules

Capsules were prepared in the conventional manner according to the following formulation.

| | |
|---|---|
| Compound 8 | 100 mg |
| Lactose | 50 mg |
| Corn starch | 47 mg |
| Crystalline cellulose | 50 mg |
| Talc | 2 mg |
| Magnesium stearate | 1 mg |
| Per one capsule | 250 mg |

Dosage Form Example 5 Syrup

A syrup was prepared in the conventional manner according to the following formulation.

| | |
|---|---|
| Compound 7 | 1 g |
| Purified sucrose | 60 g |
| Ethyl para-hydroxybenzoate | 5 mg |
| Butyl para-hydroxybenzoate | 5 mg |
| Flavor | suitable amount |
| Coloring matter | suitable amount |
| Purified water | suitable amount |
| Total amount | 100 ml |

Dosage Form Example 6 Injection

An injection was prepared in the conventional manner according to the following formulation.

| | |
|---|---|
| Compound 11 | 100 mg |
| Distilled water for injection | suitable amount |
| Per one ampoule | 2 ml |

Dosage Form Example 7 Suppositories

Suppositories were prepared in the conventional manner according to the following formulation.

| | |
|---|---|
| Compound 18 | 100 mg |
| Witepsol W-35 (registeredtrademark; a mixture of mono-, di- and triglycerides of saturated fatty acids consisting of lauric acid | 1400 mg |

| | -continued |
|---|---|
| to stearic acids; product of Dynamit Nobel Co., Ltd.) | |
| Per one suppository | 1500 mg |

Pharmacological Tests
(1) Cyclooxygenase inhibiting effect

This assay was carried out by the method described in Russell J. Taylor et al., Biochem. Pharmacol., 25, 2479–2484 (1976).

$^{14}$C-arachidonic acid was reacted with seminal vasicular gland microsomes and the test drugs at various concentrations over a predetermined period of time and the obtained prostaglandin $E_2$ was separated by thin layer chromatography. The radioactivity of prostaglandin $E_2$ was determined by liquid scintillation counter. The $IC_{50}$ values were calculated by the comparison with the radioactivity of the control.

(2) 5-Lipoxygenase inhibiting activity

This assay was carried out by the method described in Kenkichi Ochi et al., J. Biol. Chem., 258, 5754–5758 (1983).

Casein was injected into the abdominal cavity of a guinea pig, and the polymorphonuclear leucocytes were collected and the cytosol fraction was obtained as an enzyme source. $^{14}$C-arachidonic acid was reacted with the enzyme and the test drug at various concentrations over a predetermined period of time. The obtained 5-hydroxyeicosatetraenoic acid was separated by thin layer chromatography and the radioactivity was determined. The $IC_{50}$ values were calculated by the comparison with the radioactivity of the control.

The results of the above tests (1) and (2) are shown below in Table 2.

Table 2

| | $IC_{50}$ (μM) | |
|---|---|---|
| Compound No. | Cyclooxygenase | Lipoxygenase |
| 1 | 2.87 | 1.17 |
| 2 | 4.05 | 0.65 |
| 3 | 1.20 | 0.30 |
| 4 | 0.95 | 0.18 |
| 6 | 1.38 | 0.62 |
| 7 | 0.17 | 0.08 |
| 8 | 4.76 | 0.26 |
| 11 | 0.68 | 0.24 |
| 18 | 0.11 | 0.18 |
| 20 | 1.85 | 0.24 |
| 23 | 2.94 | 0.09 |

The results of Table 2 show that the compounds of the present invention potently inhibit both cyclooxygenase and lipoxygenase.

(Reference Example 1)

Synthesis of 5-(2-aminoethyl)-3,4-diphenylisoxazole

The compound mentioned above was obtained in the same manner as in example 1b using deoxybenzoin in place of deoxyanisoin. Physical properties of the compound obtained were shown below.

$^1$H-NMR (DMSO-$d_6$+$D_2$O) δ: 2.85 (m, 4H), 7.17–7.83 (m, 10H).

(Reference Example 2)

Synthesis of 5-(2-aminoethyl)-3,4-bis(4-chlorophenyl)isoxazole

The compound mentioned above was obtained in the same manner as in example 1b using 1,2-bis(4-chlorophenyl)ethanone in place of deoxyanisoin. Physical properties of the compound obtained were shown below.

$^1$H-NMR (DMSO-$d_6$+$D_2$O) δ: 2.87 (m, 4H), 7.23–7.54 (m, 8H).

(Reference Example 3)

Synthesis of 5-(2-aminoethyl)-3-(4-chlorophenyl)-4-(4-methoxyphenyl)isoxazole

The compound mentioned above was obtained in the same manner as in example 1b using 1-(4-chlorophenyl)-2-(4-methoxyphenyl)ethanone in place of deoxyanisoin. Physical properties of the compound obtained were shown below.

$^1$H-NMR (DMSO-$d_6$+$D_2$O) δ: 2.85 (m, 4H), 3.79 (s, 3H), 7.02–7.53 (m, 8H).

(Reference Example 4)

Synthesis of 5-(2-aminoethyl)-3,4-bis(4-methylphenyl)isoxazole

The compound mentioned above was obtained in the same manner as in example 1b using 1,2-(4-methylphenyl)ethanone in place of deoxyanisoin. Physical properties of the compound obtained were shown below.

$^1$H-NMR (DMSO-$d_6$+$D_2$O) δ: 2.30 (s, 3H), 2.33 (s, 3H), 2.82 (m, 4H), 7.05–7.28 (m, 8H).

The isoxazole derivatives obtained in reference examples 1–4 can be converted to the styrene derivatives of the invention by reacting them with, for example, α-ethoxycarbonyl-3,5-dimethoxy-4-hydroxycinnamic acid according to a method of example 1a).

We claim:

1. A styrene derivative represented by the formula (1) or a salt thereof:

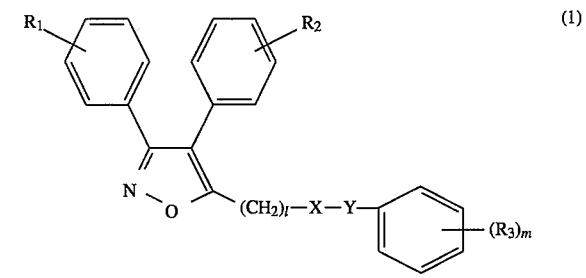

wherein $R_1$ and $R_2$ are the same or different and each is a hydrogen atom, a lower alkoxy group, a halogen atom or a lower alkyl group; $R_3$ are the same or different and each is a hydroxy group, a lower alkoxy group, a lower alkyl group, a lower alkoxycarbonyloxy group, a lower acyloxy group, a di-loweralkyl phosphate or an amino acid which may have a protective group; l is an integer of 0 to 5; m is an integer of 0 to 5; X represents a formula —N(Z)CO— {wherein Z represents a formula $(CH_2)_n$A (wherein A represents a hydrogen atom, a carboxyl group, a di- or mono-loweralkylcarbamoyl group, a carbamoyl group, a lower alkoxycarbonyl group, a cyano group, a lower alkoxy group, a N-acylamino group, a phenyl group which may be substituted, a pyridyl group or a thienyl group, n is an integer of 0 to 5)} or a single bond, Y represents —C(Z')=CH—, —CH=CH—C(Z')=CH—, —C(Z')=CH—CH=CH— (wherein Z' is the same as Z), provided that when n=0, both Z and Z' are not hydrogen atoms, and that when l is 0, X represents a single bond.

2. The styrene derivative or a salt thereof according to claim 1 wherein $R_1$ and $R_2$ are lower alkoxy groups.

3. The styrene derivative or a salt thereof according to claim 1 wherein $R_3$ are the same or different and each is a hydroxy group, a lower alkoxy group, a lower alkyl group, a lower alkoxycarbonyloxy group or a lower acyloxy group.

4. The styrene derivative or a salt thereof according to claim 1 wherein $R_3$ are the same or different and each is a hydroxy group, a lower alkoxy group or a lower alkoxycarbonyloxy group.

5. The styrene derivative or a salt thereof according to claim 1 wherein X represents —NHCO—.

6. The styrene derivative or a salt thereof according to claim 1 wherein Y represents —C(Z')═CH—, —CH═CH—C(Z')═CH— or —C(Z')═CH—CH═CH—, wherein n shown in Z' is 0 to 3, A represents a hydrogen atom, a di- or mono-loweralkylcarbamoyl group, a lower alkoxycarbonyl group, a lower alkoxy group or a thienyl group.

7. The styrene derivative or a salt thereof according to claim 1 wherein Y represents —C(Z')═CH— or —C(Z')═CH—CH═CH—, wherein n shown in Z' is 0, A represents a di- or mono-loweralkylcarbamoyl group or a lower alkoxycarbonyl group.

8. The styrene derivative or a salt thereof according to claim 1 wherein $R_1$ and $R_2$ are lower alkoxy groups; $R_3$ are the same or different and each is a hydroxy group, a lower alkoxy group, a lower alkyl group, a lower alkoxycarbonyloxy group or a lower acyloxy group; X represents —NHCO—, Y represents —C(Z')═CH—, —CH═CH—C(Z')═CH— or —C(Z')═CH—CH═CH— (wherein n shown in Z' is 0 to 3, A represents a hydrogen atom, a di- or mono-loweralkylcarbamoyl group, a lower alkoxycarbonyl group, a lower alkoxy group or a thienyl group.

9. The styrene derivative or a salt thereof according to claim 1 wherein $R_1$ and $R_2$ are lower alkoxy groups; $R_3$ are the same or different and each is a hydroxy group, a lower alkoxy group or a lower alkoxycarbonyloxy group; X represents —NHCO—, Y represents —C(Z')═CH— or —C(Z')═CH—CH═CH— (wherein n shown in Z' is 0, A represents a di- or mono-loweralkylcarbamoyl group or a lower alkoxycarbonyl group.

10. A composition for inhibiting lipoxygenase comprising an effective amount of the styrene derivative as defined in claim 1 and a pharmaceutically acceptable carrier therefor.

11. A composition for inhibiting 5-lipoxygenase comprising an effective amount of the styrene derivative as defined in claim 1 and a pharmaceutically acceptable carrier therefor.

12. A composition for inhibiting cyclooxygenase comprising an effective amount of the styrene derivative as defined in claim 1 and a pharmaceutically acceptable carrier therefor.

13. A method for inhibiting lipoxygenase which comprises administering to a patient an effective amount of the styrene derivative as defined in claim 1.

14. A method for inhibiting 5-lipoxygenase which comprises administering to a patient an effective amount of the styrene derivative as defined in claim 1.

15. A method for inhibiting cyclooxygenase which comprises administering to a patient an effective amount of the styrene derivative as defined in claim 1.

* * * * *

UNITED STATES PATENT AND TRADEMARK OFFICE
CERTIFICATE OF CORRECTION

PATENT NO. : 5,478,856
DATED : December 26, 1995
INVENTOR(S) : SUZUKI et al.

It is certified that error appears in the above-indentified patent and that said Letters Patent is hereby corrected as shown below:

On the title page,

Item [87], line 2, please delete "PCT Pub. Date: Nov. 5, 1994" insert therefor

-- PCT Pub. Date: May 11, 1994 --

Signed and Sealed this

Twentieth Day of May, 1997

Attest:

BRUCE LEHMAN

*Attesting Officer*      *Commissioner of Patents and Trademarks*